(12) United States Patent
Belaid-Choucair et al.

(10) Patent No.: US 11,629,192 B2
(45) Date of Patent: Apr. 18, 2023

(54) METHODS AND PHARMACEUTICAL COMPOSITIONS FOR THE TREATMENT OF DISEASES MEDIATED BY THE NRP-1/OBR COMPLEX SIGNALING PATHWAY

(71) Applicants: INSERM (Institut National de la Sante et de la Recherche Medicale), Paris (FR); Universite Paris Descartes, Paris (FR); Fondation Imagine, Paris (FR); Assistance Publique-Hopitaux de Paris (APHP), Paris (FR); Centre National de la Recherche Scientifique (CNRS), Paris (FR); Universite Grenoble Alpes, Saint Martin d'Heres (FR); Commissariat a l'Energie Atomique et aux Energies Alternatives, Paris (FR); Universite de Bourgogne, Dijon (FR)

(72) Inventors: Zakia Belaid-Choucair, Paris (FR); Olivier Hermine, Paris (FR); Carmen Garrido-Fleury, Dijon (FR); Claude Cochet, Grenoble (FR); Odile Filhol-Cochet, Grenoble (FR); Renaud Seigneuric, Dijon (FR)

(73) Assignees: INSERM (INSTITUT NATIONAL DE LA SANTE ET DE LA RECHERCHE MEDICALE), Paris (FR); UNIVERSITÉ PARIS CITÉ, Paris (FR); FONDATION IMAGINE, Paris (FR); ASSISTANCE PUBLIQUE-HOPITAUX DE PARIS (APHP), Paris (FR); CENTRE NATIONAL DE LA RECHERCHE SCIENTIFIQUE (CNRS), Paris (FR); UNIVERSITE GRENOBLE ALPES, Saint-Martin-d'Hères (FR); COMMISSARIAT A L'ENERGIE ATOMIQUE ET AUX ENERGIES ALTERNATIVES, Paris (FR); UNIVERSITE DE BOURGOGNE, Dijon (FR)

( * ) Notice: Subject to any disclaimer, the term of this patent is extended or adjusted under 35 U.S.C. 154(b) by 255 days.

(21) Appl. No.: 16/120,514

(22) Filed: Sep. 4, 2018

(65) Prior Publication Data
US 2019/0002569 A1   Jan. 3, 2019

Related U.S. Application Data

(62) Division of application No. 15/119,401, filed as application No. PCT/EP2015/053355 on Feb. 18, 2015, now abandoned.

(30) Foreign Application Priority Data

Feb. 18, 2014   (EP) .................... 14305220

(51) Int. Cl.
| | | |
|---|---|---|
| A61K 31/00 | (2006.01) | |
| A61K 39/00 | (2006.01) | |
| C07K 16/28 | (2006.01) | |
| A61K 38/17 | (2006.01) | |
| A61K 31/4745 | (2006.01) | |
| A61K 31/7105 | (2006.01) | |
| A61K 31/713 | (2006.01) | |
| A61K 39/395 | (2006.01) | |
| A61K 45/06 | (2006.01) | |

(Continued)

(52) U.S. Cl.
CPC ...... *C07K 16/2863* (2013.01); *A61K 31/4745* (2013.01); *A61K 31/713* (2013.01); *A61K 31/7105* (2013.01); *A61K 38/17* (2013.01); *A61K 39/39558* (2013.01); *A61K 45/06* (2013.01); *C12N 15/1138* (2013.01); *G01N 33/566* (2013.01); *C07K 2317/76* (2013.01); *C12N 2310/14* (2013.01); *C12N 2310/531* (2013.01); *C12N 2320/31* (2013.01); *G01N 2333/70503* (2013.01); *G01N 2333/71* (2013.01); *G01N 2500/02* (2013.01); *Y02A 50/30* (2018.01)

(58) Field of Classification Search
CPC .......... C07K 16/2863; A61K 39/39558; A61K 38/17; C12N 15/1138; G01N 33/566
See application file for complete search history.

(56) References Cited

U.S. PATENT DOCUMENTS

2011/0142815 A1*  6/2011  Yu .................... A61P 43/00
                                                424/94.1

FOREIGN PATENT DOCUMENTS

WO    WO2011089101    *    7/2011

OTHER PUBLICATIONS

Siddiqui-Jain et al (Cancer Res 70:10288, Dec. 2010 (Year: 2010).*

(Continued)

*Primary Examiner* — Lei Yao
(74) *Attorney, Agent, or Firm* — WC&F IP

(57) ABSTRACT

The present invention relates to methods and pharmaceutical compositions for the treatment of diseases mediated by the NRP-1/OBR complex signaling pathway. In particular, the present invention relates to a method for treating a disease selected from the group consisting of cancers, obesity and obesity related diseases, anorexia, autoimmune diseases and infectious diseases in a subject in need thereof comprising administering the subject with a therapeutically effective amount of an antagonist of the NRP-1/OBR signaling pathway.

4 Claims, 9 Drawing Sheets

Figure 1A:
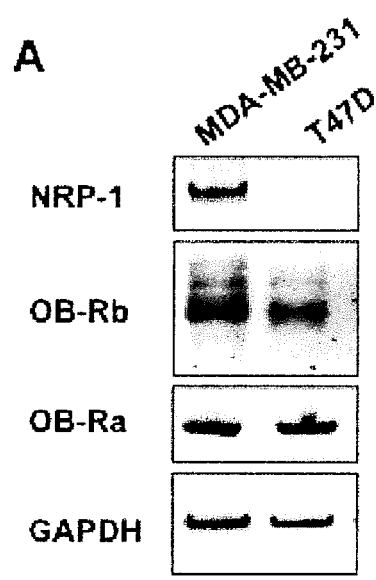
Figure 1B:
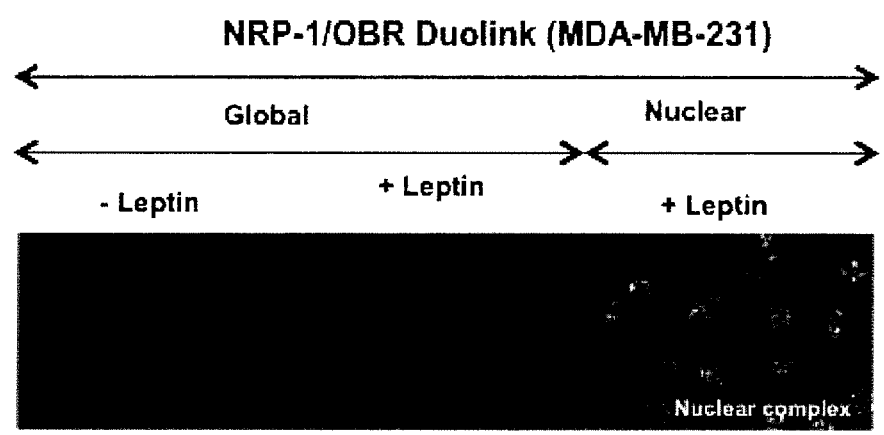
Figure 1C:
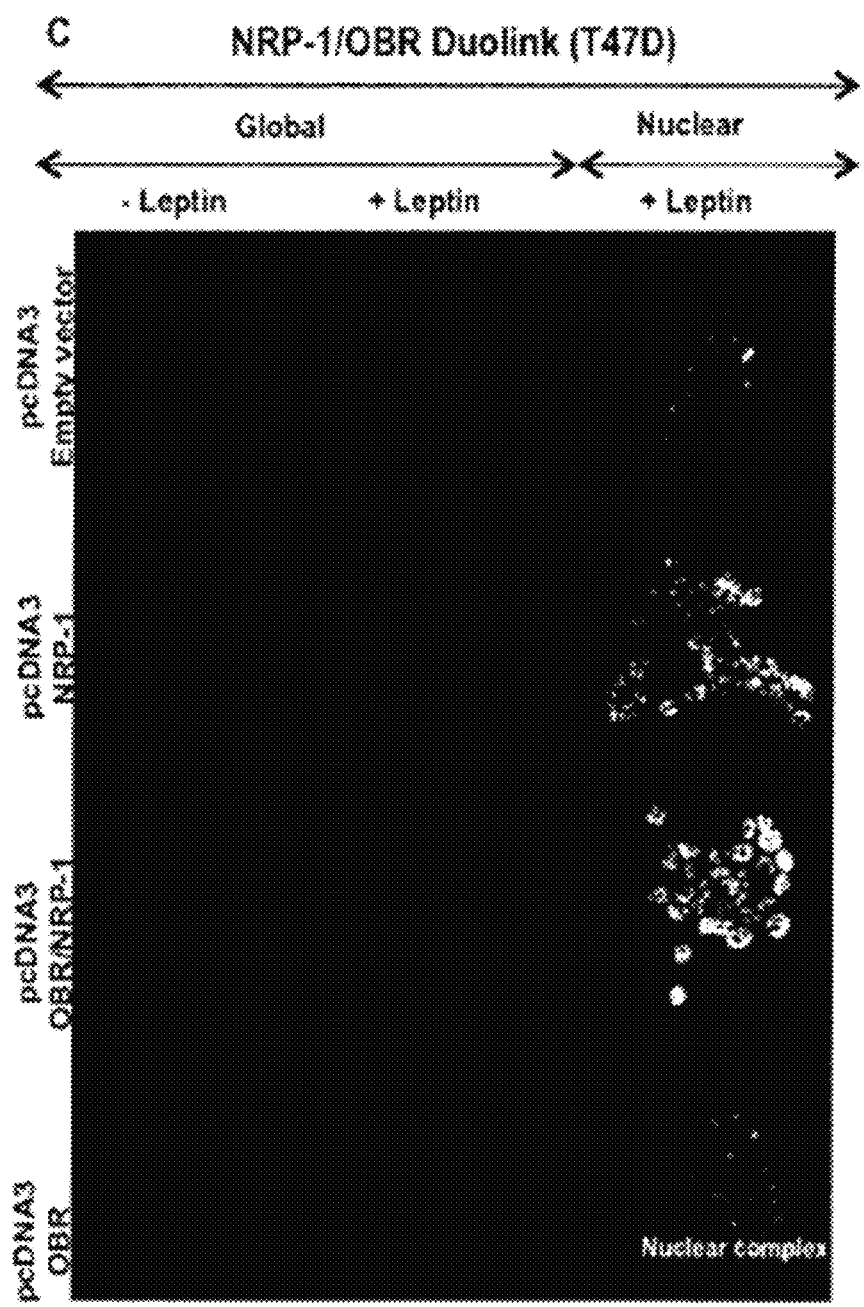
Figure 1D:
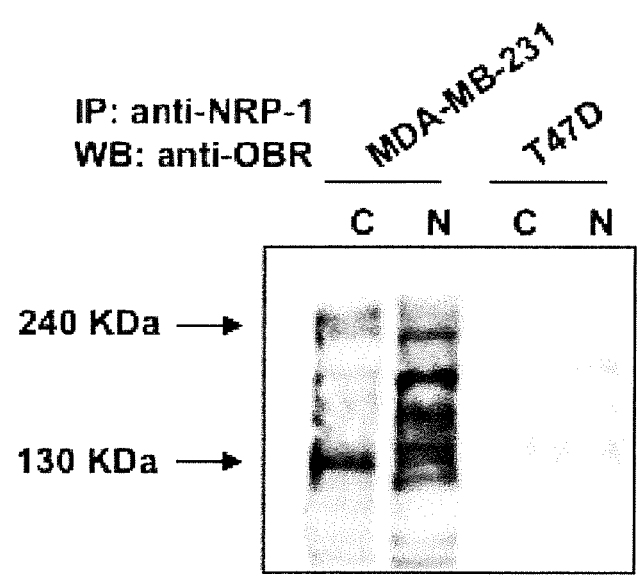
Figures 2A, 2B, 2C:
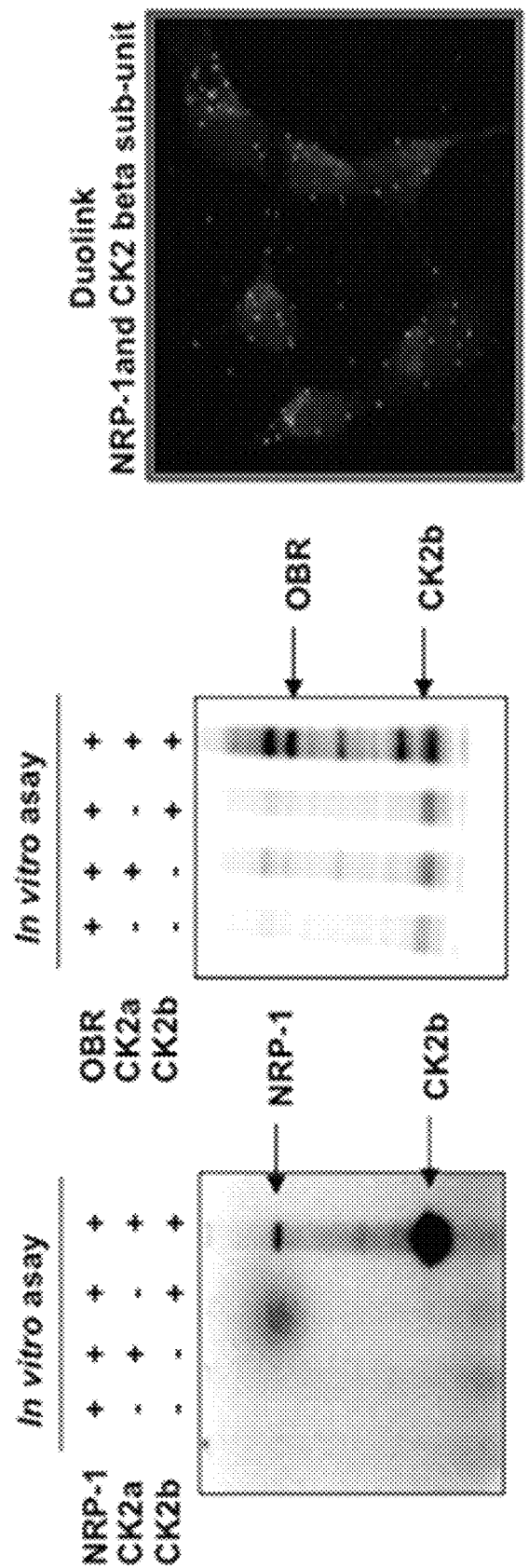
Figures 2D, 2E:
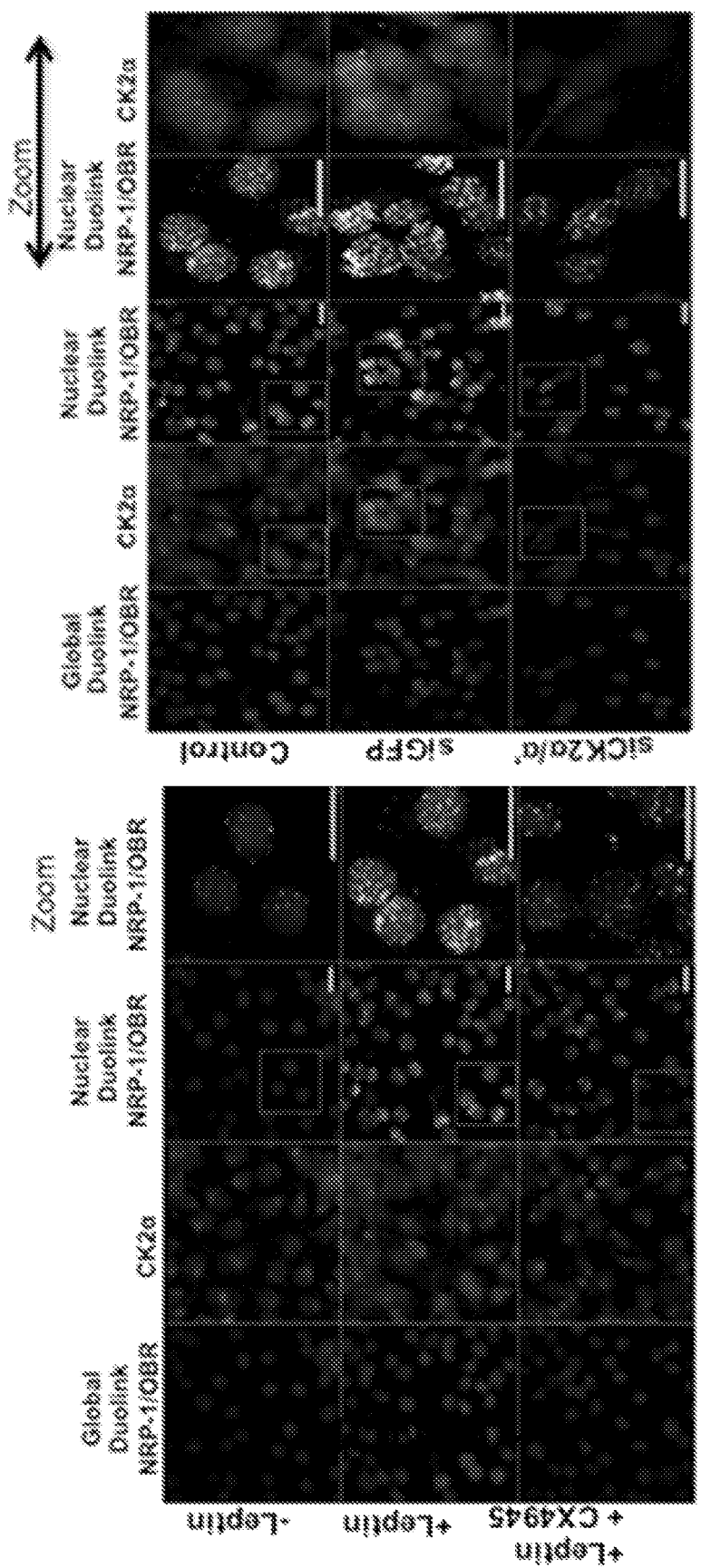

(51) Int. Cl.
*C12N 15/113* (2010.01)
*G01N 33/566* (2006.01)

(56) References Cited

OTHER PUBLICATIONS

Human protein Atlas (Year: 2020).*
Hung et al, Inter J Onco 43:1517-1522, online published Sep. 4, 2013 (Year: 2013).*
Moucadel et al (Oncotarget 2: 997-1010, 2011 (Year: 2011).*
Ahmad et al, Advanceds in Enzym Regulation 48:179-187, 2008 (Year: 2008).*

* cited by examiner

METHODS AND PHARMACEUTICAL COMPOSITIONS FOR THE TREATMENT OF DISEASES MEDIATED BY THE NRP-1/OBR COMPLEX SIGNALING PATHWAY

FIELD OF THE INVENTION

The present invention relates to methods and pharmaceutical compositions for the treatment of diseases mediated by the NRP-1/OBR complex signaling pathway.

BACKGROUND OF THE INVENTION

Neuropilin-1 (NRP-1) a trans-membrane receptor that plays a central role in neuronal development (Fujisawa et al., 1995) has been subsequently shown to be also involved in blood vessel development as a co-receptor for two different types of ligands, the semaphorin (SEMA) family of axon guidance modulators and the vascular endothelial growth factor (VEGF) family of angiogenesis stimulators, respectively. NRP-1 needs to form complexes with receptors belonging to the plexin family, which serve as the signal-transducing element for the axonal repulsion and collapse of neuronal growth cones after SEMA binding to the NRP-1/plexin complex (He and Tessier-Lavigne, 1997). NRP-1 also interacts as well with VEGF receptors (VEGFR) forming a complex, which can be activated by VEGF-A165 for normal developmental angiogenesis (Soker et al., 1998). In addition, it has been shown that NRP-1 plays a critical role in the regulation of the immune system by modulating interactions between dendritic and T cells in the periphery and between thymocytes and thymic epithelial cells in the thymus (Tordjman et al, 2002) (Lepelletier et al., 2007). Amongst these normal physiologic functions NRP-1 is also involved in physiopathology. For example, NRP-1 is a receptor for the HTLV-1 virus (Ghez et al., 2006). In addition, data are accumulating showing that NRP-1 is involved in oncogenesis (Soker et al., 2001; Ellis et al, 2006), but its role remains controversial. SEMA inhibit cell growth and decrease cell survival by inducing PTEN activity, an inhibitor of the PI3kinase pathway (Cantly et al., 1999), whereas VEGF plays an opposite role by competing with SEMA for binding to NRP-1 and by providing signaling for cell proliferation and survival through NRP-1/VEGFR complex (Bachelder et al., 2003; Narazaki and Tosato, 2006). In some cancer cells, including breast cancer cells, the expression of NRP-1 increases cell proliferation and invasiveness through mechanisms that do not necessarily involved neither SEMA nor VEGF suggesting that alternative ligands and/or receptors may use NRP-1 as a co-receptor (Kigel et al., 2008).

Leptin is a small non glycosylated protein expressed not only by the benign primary source adipocytes but by cancer cells also (Clin Cancer Research 2004). OBR is the receptor of leptin. Leptin has been shown to regulate gene expression. More than 64 genes were identified including those for growth, cell cycle regulators, extracellular matrix proteins and gene associated with metastasis (J of Endocrinol 2008; EBM 2008). Obesity is considered a risk for many cancers. Serum leptin levels are often elevated in obese people. Leptin acts as a mitogenic agent in many tissues; therefore, it may act to promote cancer cell growth. In fact, leptin was shown to act as a growth factor for prostate cancer cells in vitro, to induce increased migration of prostate cancer cells and expression of growth factors such as vascular endothelial growth factor (VEGF), transforming growth factor-beta 1 (TGF-β1), and basic fibroblast growth factor (bFGF), and to enhance prostate cancer growth. Leptin has been shown recently to promote T helper 1 (Th1)-cell differentiation and to modulate the onset and progression of autoimmune responses in several animal models of disease. If leptin's role is fundamental in Th1-mediated autoimmune diseases or inflammatory diseases, such as inflammatory bowel syndrome, then a therapeutic effect can be anticipated by blocking peripheral leptin action. Leptin has also been shown to be involved in the pathogenesis of rheumatoid arthritis and in the development of experimental autoimmune encephalomyelitis (EAE), a mouse model for multiple sclerosis. Consequently, inhibitors of the leptin signaling pathway are highly desirable for therapeutic purposes.

SUMMARY OF THE INVENTION

The present invention relates to methods and pharmaceutical compositions for the treatment of diseases mediated by the NRP-1/OBR complex signaling pathway. In particular, the present invention is defined by the claims.

DETAILED DESCRIPTION OF THE INVENTION

Several studies have demonstrated Neuropilin-1 (NRP-1) implication in tumor progression independently of its known co-receptors and cognate ligands. On the basis of growing connections between breast cancer and obesity, and Leptin and its receptor OBR involved in this process the inventors postulated that NRP-1 is a new target of treatment of breast cancer and by extension other cancer in which OBR and Leptin are involved. In addition inhibition of VEGF interaction (for example with Avastin) with its cognate receptor and NRP-1 may favor increase signaling with Leptin with NRP-1/OBR receptor complex resulting in an increase of metastasis and shortening overall survival.

By using a well described MDA-MB231 (NRP-1 positive and OBR positive) and T47D (OBR low and NRP-1 negative) breast cancer cell lines model transduced either by shNRP-1 or cDNA encoding for NRP-1 the inventors have shown that:

1) In vitro Leptin decreased cell proliferation and increased migration and these effects were dependent on NRP-1 expression. In vivo studies on xenograft models either by overexpressing NRP-1 in T47D or by silencing NRP-1 in MDA-MB231 have also shown a correlation between NRP-1 expression and lymph node infiltration and this infiltration increased with tumor treatment with leptin
2) NRP-1 forms a complex with OBR
3) the NRP-1/OBR complex formation is leptin dependent
4) the NRP-1/OBR complex translocates to the nucleus
5) the NRP-1/OBR complex formation and nuclear translocation are dependent on NRP-1 and OBR phosphorylation by the Serine/threonine Protein-kinase CK2 (CK2). This was confirmed by the inhibition of CK2 by 3 different chemical compounds (TBB, DRB and CX4945) and by RNA silencing that prevented not only NRP-1 and OBR phosphorylation but also the formation and the nuclear translocation of the NRP-1/OBR complex.
6) As other known NRP-1 ligands (VEGF, Sema3A, TGFβ and PDGF), NRP-1 does bind directly to leptin and induces OBR oligomerization upon leptin binding to OBR. The oligomerization results in OBR signaling increase. This last result show that leptin can a be targeted as a true NRP-1 ligand to prevent its binding as it was the case for VEGF and SEMA to block metastasis induced by NRP-1/OBR complex.

Accordingly, the characterization of the NRP-1/OBR complex and its nuclear translocation shed a light on an eventual function of NRP-1 as transcription factor or activator since the inventors detected NRP-1/OBR complex in the nucleus and NRP-1 Chip-Seq analysis of sample generated from MDA-MB-231 led to identify genes implicated in metabolism, in immune cell response and breast cancer metastasis and with enriched sequences containing RNA polymerase II (Pol2) and transcription factor binding sites. This was confirmed by the detection of NRP-1and Pol2 interaction.

The new complex NRP-1/OBR, its phosphorylation by CK2, its identification as nuclear receptor and the association of NRP-1 with RNA polymerase II thus open a wide field of investigations for the understanding of the metabolism and metabolism-associated disorders, mainly obesity and anorexia, leading thus to new therapeutic strategies such as the use of CK2 inhibitors.

Accordingly a first aspect of the invention relates to a method for treating a disease selected from the group consisting of cancers, obesity and obesity related diseases, cachexia, anorexia, ureteral obstructive kidney disease, autoimmune diseases and infectious diseases in a subject in need thereof comprising administering the subject with a therapeutically effective amount of an antagonist of the NRP-1/OBR signaling pathway.

As used herein, the terms "treatment," "treat," and "treating" refer to reversing, alleviating, inhibiting the progress of a disease or disorder as described herein, or delaying, eliminating or reducing the incidence or onset of a disorder or disease as described herein, as compared to that which would occur in the absence of the measure taken. The terms "prophylaxis" or "prophylactic use" and "prophylactic treatment" as used herein, refer to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease.

The term "obesity" refers to a condition characterized by an excess of body fat. The operational definition of obesity is based on the Body Mass Index (BMI), which is calculated as body weight per height in meter squared (kg/m$^2$). Obesity refers to a condition whereby an otherwise healthy subject has a BMI greater than or equal to 30 kg/m$^2$, or a condition whereby a subject with at least one co-morbidity has a BMI greater than or equal to 27 kg/m$^2$. An "obese subject" is an otherwise healthy subject with a BMI greater than or equal to 30 kg/m$^2$ or a subject with at least one co-morbidity with a BMI greater than or equal 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$. The increased risks associated with obesity may occur at a lower BMI in people of Asian descent. In Asian and Asian-Pacific countries, including Japan, "obesity" refers to a condition whereby a subject with at least one obesity-induced or obesity-related co-morbidity that requires weight reduction or that would be improved by weight reduction, has a BMI greater than or equal to 25 kg/m$^2$. An "obese subject" in these countries refers to a subject with at least one obesity-induced or obesity-related co-morbidity that requires weight reduction or that would be improved by weight reduction, with a BMI greater than or equal to 25 kg/m$^2$. In these countries, a "subject at risk of obesity" is a person with a BMI of greater than 23 kg/m2 to less than 25 kg/m$^2$.

The method of the invention is particularly suitable for the prophylactic treatment of obesity related disorders.

The term "obesity-related diseases" encompasses disorders that are associated with, caused by, or result from obesity. Examples of obesity-related disorders include overeating and bulimia, diabetes, hypertension, elevated plasma insulin concentrations and insulin resistance, dyslipidemia, hyperlipidemia, breast, prostate, endometrial and colon cancer, heart disease, cardiovascular disorders, abnormal heart rhythms and arrhythmias, myocardial infarction, congestive heart failure, coronary heart disease, angina pectoris, cerebral infarction, cerebral thrombosis and transient ischemic attack, and osteoarthritis. Other examples include pathological conditions showing reduced metabolic activity or a decrease in resting energy expenditure as a percentage of total fat-free mass. Further examples of obesity-related disorders include metabolic syndrome, also known as syndrome X, insulin resistance syndrome, type II diabetes, impaired fasting glucose, impaired glucose tolerance, inflammation, such as systemic inflammation of the vasculature, atherosclerosis, hypercholesterolemia, hyperuricaemia, as well as secondary outcomes of obesity such as left ventricular hypertrophy. Obesity-related disorders also include the liver abnormalities associated with obesity such as non-alcoholic fatty liver disease (NAFLD) a rising cause of cirrhosis associated to obesity and metabolic syndrome. Indeed, NAFLD can present as simple steatosis or evolve towards inflammation and steatohepatitis (NASH), with a 20% risk of cirrhosis after 20 years. "Dyslipidemia" is a major risk factor for coronary heart disease (CHD). Low plasma levels of high density lipoprotein (HDL) cholesterol with either normal or elevated levels of low density (LDL) cholesterol is a significant risk factor for developing atherosclerosis and associated coronary artery disease in humans. Dyslipidemia is often associated with obesity.

As used herein, the term "cancer" has its general meaning in the art and includes, but is not limited to, solid tumors and blood borne tumors The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

"Autoimmune diseases" in the context of the present invention, relates to diseases arising from an overactive immune response of the body against substances and tissues normally present in the body. In other words, the body actually attacks its own cells or components. The immune system mistakes some part of the body as a pathogen and attacks it. This may be restricted to certain organs (e.g. in thyroiditis) or involve a particular tissue in different places (e.g. Goodpasture's disease which may affect the basement membrane in both the lung and the kidney). The treatment of autoimmune and/or inflammatory diseases is typically with immunosuppression-medication which decreases the immune response. Example of autoimmune and/or inflammatory disease include but are not limited to sarcoidosis, Ankylosing Spondylitis, Crohns Disease (one of two types of idiopathic inflammatory bowel disease "IBD"), Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, systemic Lupus erythematosus, Mixed Connective Tissue Disease, Multiple Sclerosis Myasthenia gravis, Myositis, Narcolepsy, Pemphigus vulgaris, Pernicious anaemia, Psoriasis, Psoriatic Arthritis, Polymyositis, Primary biliary cirrhosis, Relapsing polychondritis, Rheumatoid arthritis, Systemic sclerosis, Temporal arteritis (also known as "giant cell arteritis"), Ulcerative Colitis (one of two types of idiopathic inflammatory bowel disease "IBD"), Vasculitis, Wegener's granulomatosis.

Typically infectious diseases include but are not limited to chronic infectious diseases and more preferably viral infections, e.g. Herpes (HSV), HIV, Hepatitis B, Hepatitis C, etc., intracellular bacterial infections, e.g. tuberculosis, salmonellosis, listeriosis, etc., and parasite infections, e.g. malaria, leishmaniasis, schistosomiasis.

As used herein, the term "NRP-1" has its general meaning in the art and refers to Neuropilin-1. Neuropilins are 120 to 130 kDa non-tyrosine kinase receptors. There are multiple NRP-1 and NRP-2 splice variants and soluble isoforms. The basic structure of neuropilins comprises five domains: three extracellular domains (a1a2, b1b2 and c), a transmembrane domain, and a cytoplasmic domain. The a1a2 domain is homologous to complement components C1r and C1s (CUB), which generally contains four cysteine residues that form two disculfid bridges. The b1b2 domain is homologous to coagulation factors V and VIII. The central portion of the c domain is designated as MAM due to its homology to meprin, AS and receptor tyrosine phosphotase $\mu$ proteins. The a1a2 and b1b2 domains are responsible for ligand binding, whereas the c domain is critical for homodimerization or heterodimerization.

As used herein the term "OBR" has its general meaning in the art and refers to the leptin receptor also known as LEPR and CD295. The human transmembrane receptor has at least four different isoforms with different C-terminus cytoplasmatic domains (Barr et al., 1999, J. Biol. Chem. 274 (30): 21416-21424). The full form of ObR (ObR1) is 1,165 amino acids long and contains extracellular, transmembrane and intracellular domains. The extracellular domain binds ligand, whereas the intracellular tail recruits and activates signaling substrates.

As used herein the term "NRP-1/OBR complex" refers to the complex resulting from the heterodimerization between NRP-1 and OBR as described in the EXAMPLE. The formation of the complex is mediated by the binding of leptin to OBR and NRP-1. The NRP-1/OBR complex formation and nuclear translocation are dependent on NRP-1 and OBR phosphorylation by the Serine/threonine Proteinkinase CK2. As described in the EXAMPLE, the NRP-1/OBR complex translocates to the nucleus and interacts with RNA polymerase II (RNApol2) so as to trigger the expression of various genes. In particular, in cancer cells, the complex triggers the expression of genes implicated in cancer metastasis. All the effects mediated by the formation of the NRP-1/OBR complex are referred as the "NRP-1/OBR/Leptin signaling pathway".

The term "antagonist of the NRP-1/OBR signaling pathway" means any compound that attenuates signal transduction mediated by the formation of the NRP-1/OBR complex as described in the EXAMPLE. In particular the antagonist of the NRP-1/OBR signaling pathway is a compound that inhibits, reduces, abolishes or otherwise reduces the formation of said complex. In other terms the antagonist of the NRP-1/OBR signaling pathway is a compound that inhibits, reduces, abolishes or otherwise reduces the signaling pathway triggered by the formation of the complex. Such inhibition may result where: (i) the antagonist of the NRP-1/OBR signaling pathway of the invention binds to NRP-1 or OBR without triggering signal transduction, to reduce or block the formation of the NRP-1/OBR complex; (ii) the antagonist of the NRP-1/OBR signaling pathway inhibits the stability of the NRP-1/OBR complex by impeding the phosphorylation mediated by the Protein-kinase CK2; or (iii) the antagonist of the NRP-1/OBR signaling pathway binds to, or otherwise inhibits the activity of, a molecule that is part of a regulatory chain that, when not inhibited, has the result of stimulating or otherwise facilitating the signal transduction mediated by the NRP-1/OBR complex.

Typically, the antagonist of the NRP-1/OBR signaling pathway includes but is not limited to an antibody, a small organic molecule, a polypeptide and an aptamer.

In some embodiments, the antagonist of the NRP-1/OBR signaling pathway is a small organic molecule.

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

In a particular embodiment, the antagonist of the NRP-1/OBR signaling pathway is a CK2 inhibitor.

CK2 inhibitors are commonly classified into three categories: (1) inhibitors that target the regulatory subunit of CK2 (e.g., genetically selected peptide aptamers); (2) inhibitors of the catalytic activity of CK2 (e.g., quinobene, TBB, DMAT, IQA); and (3) disruptors of CK2 holoenzymes, which are often molecules binding to the CK2 subunit interface and inhibit the high affinity interaction of its subunits. The CK2 inhibitors of each class can be any type of molecule, such as, small molecules, functional nucleic acids, or peptide mimetics, etc. Typically, CK2 inhibitors consist of a diverse array of chemicals, including flavonoids (e.g. apigenin), derivatives of hydro xyantraquinones/xantenones (e.g., emodin), derivatives of hydroxycoumarines (e.g., DBC), derivatives of tetrabromotriazole/imidazole (e.g., DRB, TBB, DMAT, TBCA, TBBz), and derivatives of indoloquinazolines (e.g., IQA). More particularly, many ATP-competitive inhibitors of CK2 have been reported in the literature, including 5,6-dichloro-1-P-D-ribofuranosyl-benzimidazole (D B), 6-methyl-1,3,8-trihydroxyanthraquinone (emodin), 2-dimethylamino-4,5,6,7-tetrabromo-1H-benzimidazole (DMAT), 4,5,6,7-tetrabromobenzotriazole (TBB), resorufin, 4,4',5,5',6,6'-Hexahydroxydiphenic acid 2,6,2',6'-dilactone (ellagic acid), [5-oxo-5,6-dihydroindolo-(1,2-a)quinazolin-7-yl]acetic acid (IQA), and 2-(3,4-dihydroxyphenyl)-3,5,7-trihydroxy-4H-chromen-4-one (quercetin). See, e.g., Zhu et al., 2009, Mol. Cell. Biochem. 333: 159-67; Lopez-Ramos et al., 2010, Faseb J. 24: 3171-85; and Cozza et al, 2010, Med. Res. Rev. 30: 419-62.

CK2 inhibitors as described herein also include, but are not limited to, the compounds of any of the formulae described in International Patent Application Nos. PCT/US2007/077464, PCT/US2008/074820, and PCT7US2009/035609, and U.S. Provisional Application Ser. Nos. 61/170,468 (filed 17 Apr. 2009), 61/242,227 (filed 14 Sep. 2009), 61,180,090 (filed 20 May 2009), 61/218,318 (filed 18 Jun. 2009), 61/179,996 (filed 20 May 2009), 61/218,214 (filed 14 Jun. 2009), 61/41,806 (11 Sep. 2009), 61/180,099 (filed 20 May 2009), 61/218,347 (filed 18 Jun. 2009), 61/237,227 (filed 26 Aug. 2009), 61/243,107 (filed 16 Sep. 2009) and 61/243,104 (filed 16 Sep. 2009), the contents of each of which are incorporated herein by reference in their entirety. CK2 inhibitors can be synthesized by methods known in the art, including methods disclosed in International Patent Application Nos. PCT/US2007/077464, PCT/US2008/074820, and PCT/US2009/035609.

In some embodiments, the CK2 inhibitors is selected from the group consisting of:

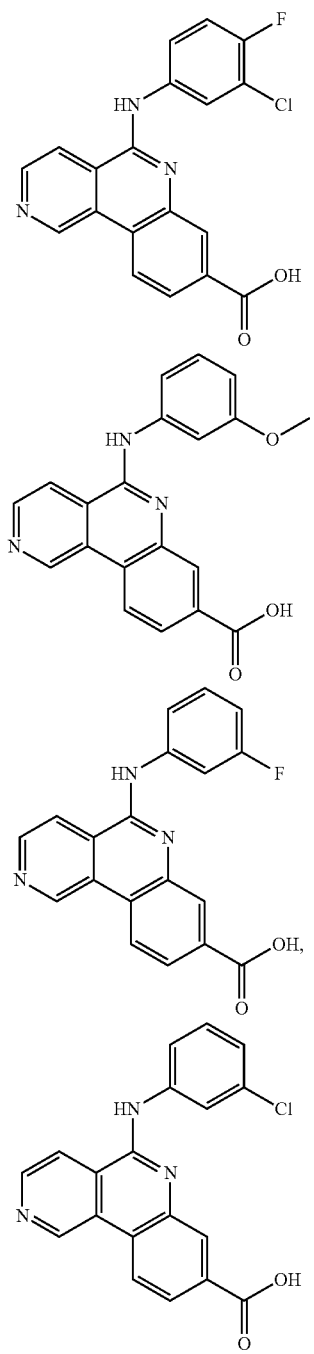

-continued
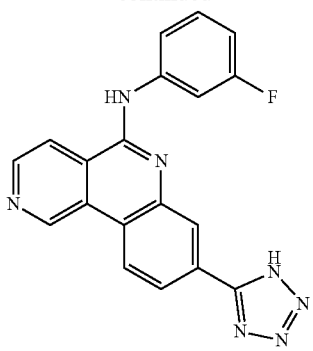
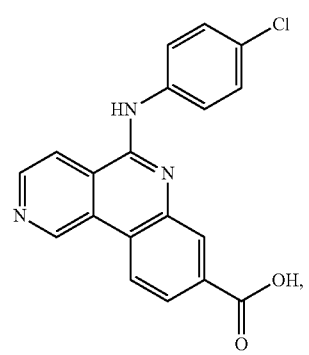
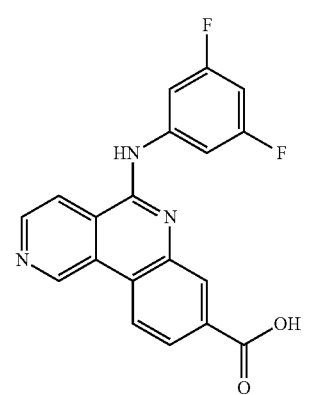
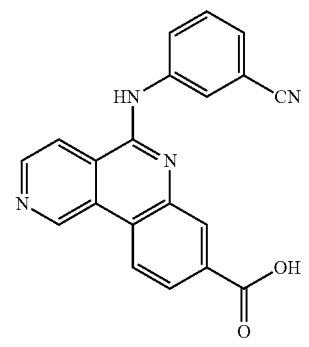
-continued
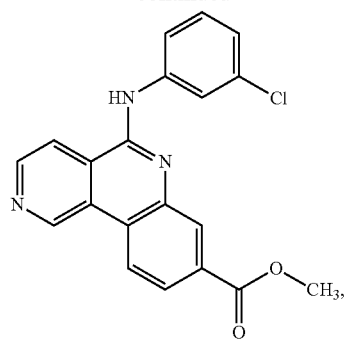
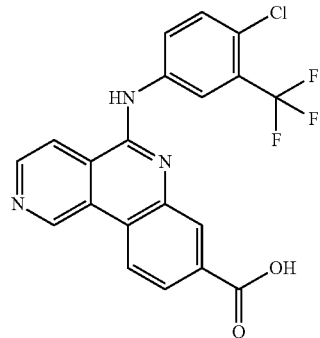
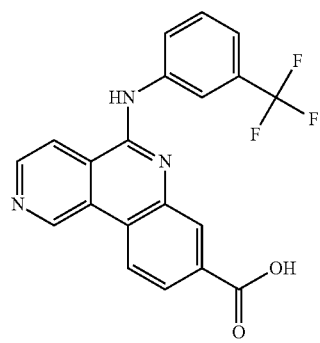
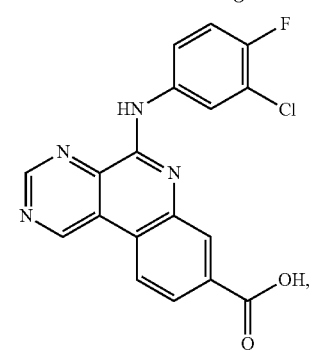
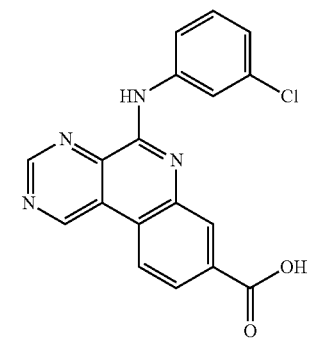

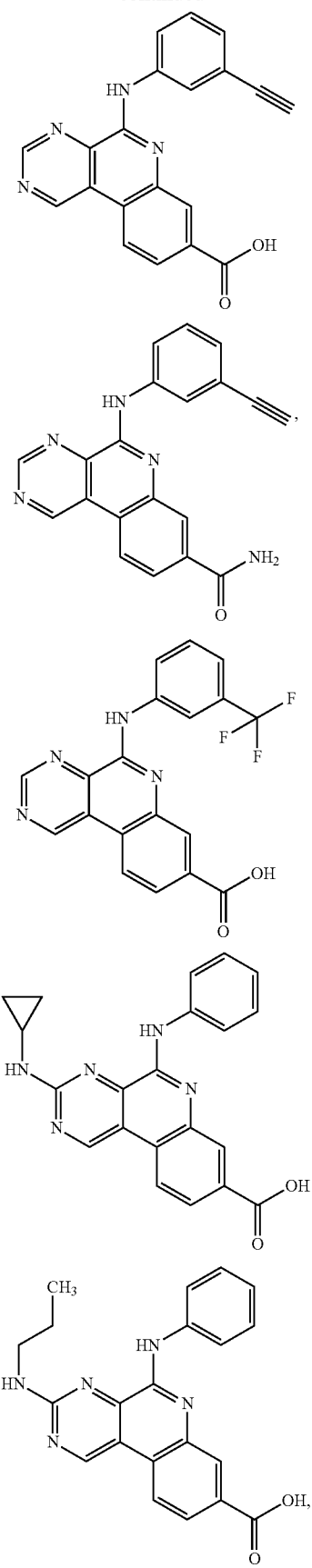
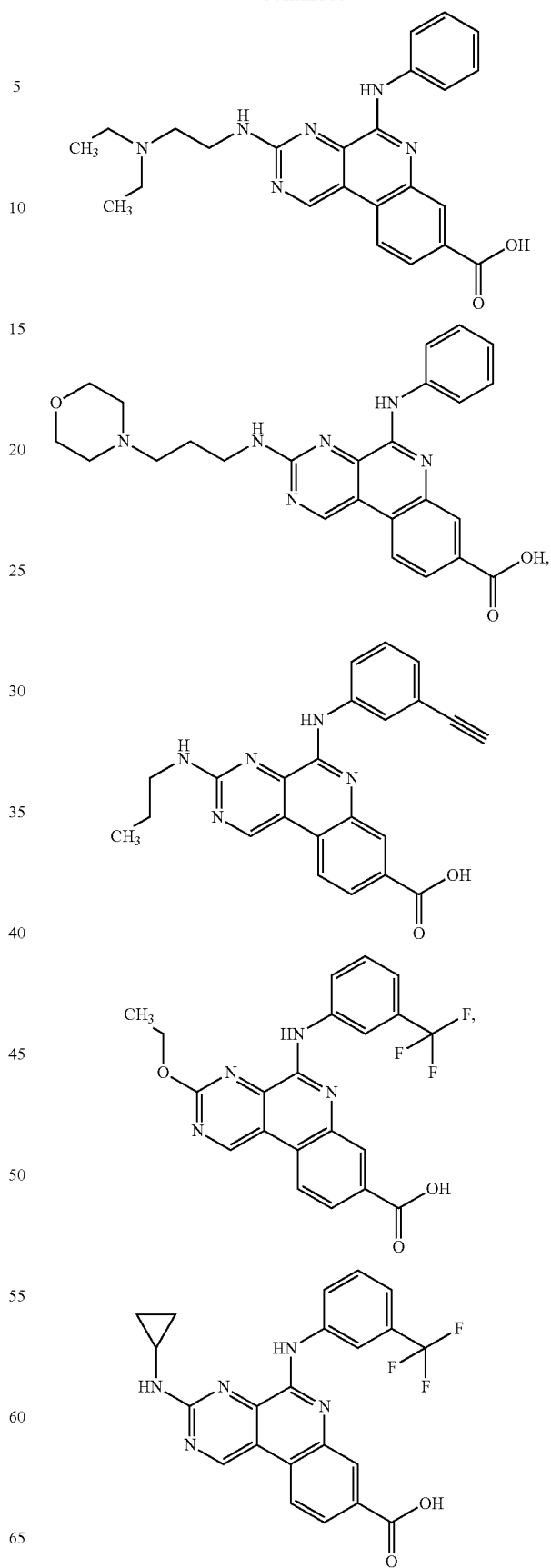

-continued

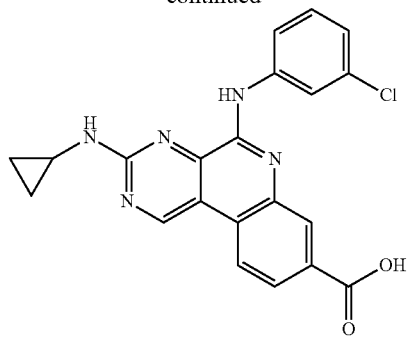

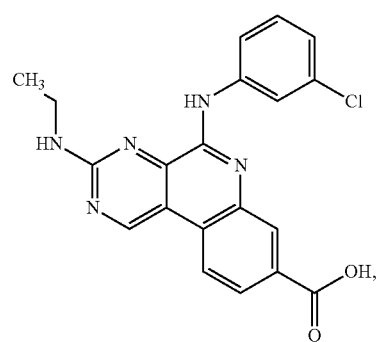

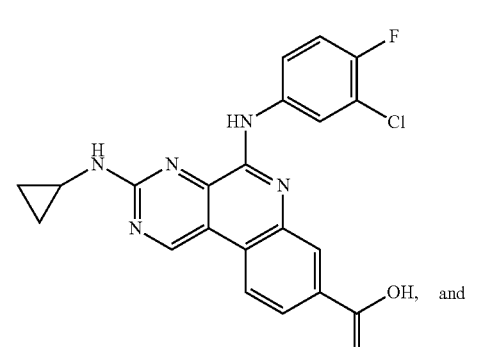

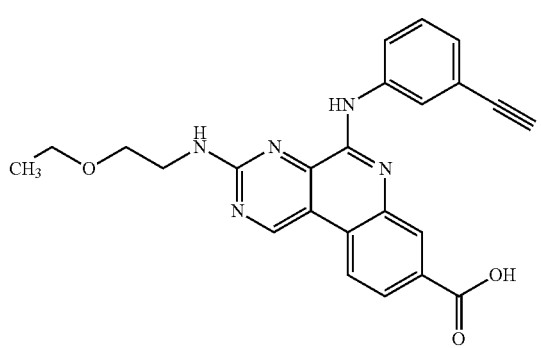

In some embodiments, the CK2 inhibitor is CX-4945:

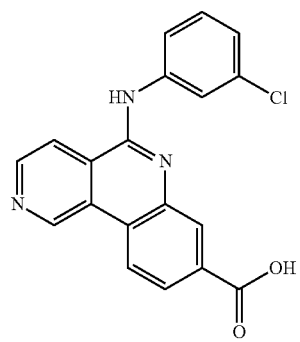 [SMILES: O=C(O)c1ccc2c(c1)nc(Nc1cccc(Cl)c1)c1ccncc12]

CX-4945 is a first-in-class potent, selective and orally available ATP-competitive inhibitor of CK2 with favorable drug properties (Siddiqui-Jain A, Bliesath J, Macalino D, Omori M, Huser N, Streiner N, Ho C B, Anderes K, Proffitt C, O'Brien S E, Lim J K, Von Hoff D D, Ryckman D M, Rice W G, Drygin D. CK2 inhibitor CX-4945 suppresses DNA repair response triggered by DNA-targeted anticancer drugs and augments efficacy: mechanistic rationale for drug combination therapy. Mol Cancer Ther. 2012 April; 11(4): 994-1005. doi: 10.1158/1535-7163.MCT-11-0613. Epub 2012 Jan. 20.).

In some embodiments, the CK2 inhibitor is a compound (Compound 1 or Compound 2) having the formula:

(1)

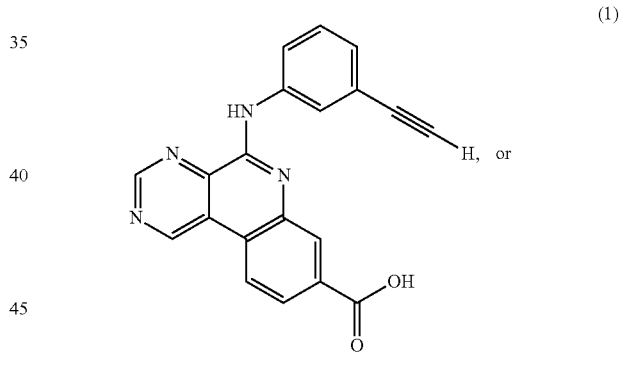

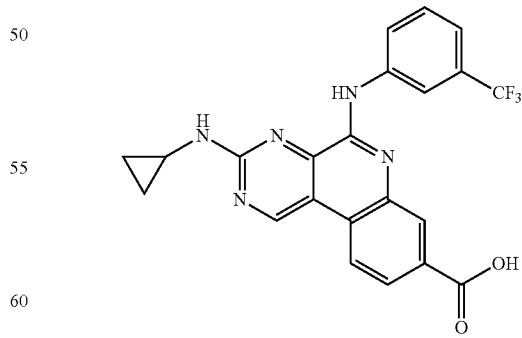

or a pharmaceutically acceptable salt or ester thereof.

In some embodiments, the CK2 inhibitor a compound described in WO 2011/013002 and in particular is selected from the group consisting of:

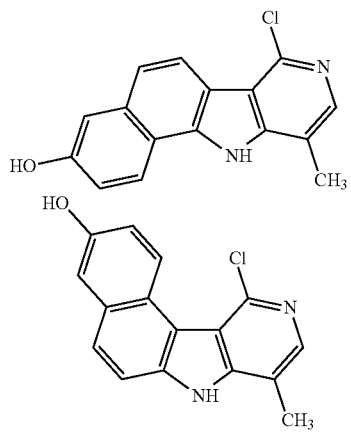

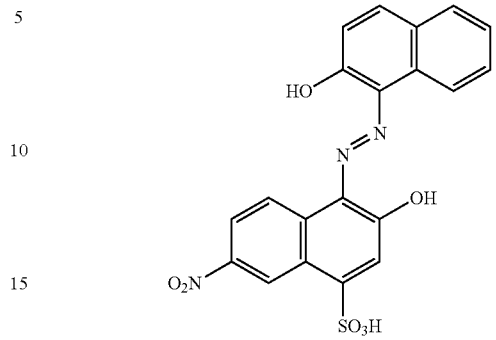

and pharmaceutically acceptable salts or esters thereof.

In some embodiments, the CK2 inhibitor is a compound as described in:

Maksym O. Chekanov, Olga V. Ostrynska, Sergii S. Tarnayskyi, Anatoliy R. Synyugin, Nadiia V. Briukhovetska, Volodymyr G. Bdzhola, Alexander E. Pashenko, Andrey A. Fokin, Sergiy M. Yarmoluk Design, synthesis and biological evaluation of 2-aminopyrimidinones and their 6-aza-analogs as a new class of CK2 inhibitors Journal of Enzyme Inhibition and Medicinal Chemistry Maksym O. Chekanov, Olga V. Ostrynska, Anatoliy R. Synyugin, Volodymyr G. Bdzhola, Sergiy M. Yarmoluk Design, synthesis and evaluation of 2-phenylisothiazolidin-3-one-1,1-dioxides as a new class of human protein kinase CK2 inhibitors Journal of Enzyme Inhibition and Medicinal Chemistry Posted online on 11 Apr. 2013.

Giorgio Cozza, Lorenzo A Pinna, Stefano Moro Protein kinase CK2 inhibitors: a patent review Expert Opinion on Therapeutic Patents September 2012, Vol. 22, No. 9, Pages 1081-1097.

In some embodiments, the CK2 inhibitor is an allosteric CK2 inhibitor, i.e. a compound which does not compete with ATP but still inhibits CK2 by modifying the conformation of a CK2 subunit (e.g. CK2 alpha) in manner that the enzyme is inactive. Examples of allosteric CK2 inhibitors include but are not limited to Azonaphthalene derivatives (compound M4) as described in Moucadel V, Prudent R, Sautel C F, Teillet F, Barette C, Lafanechere L, Receveur-Brechot V, Cochet C. Antitumoral activity of allosteric inhibitors of protein kinase CK2. Oncotarget. 2011 December; 2(12): 997-1010. Another example includes D3.1 as described in the EXAMPLE.

In some embodiments, the allosteric CK2 inhibitor is D3.1 which has the general formula of:

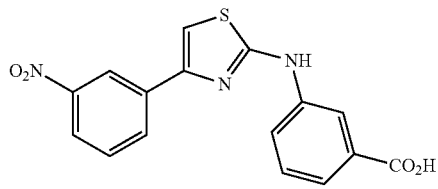

In some embodiments, the allosteric CK2 inhibitor is M4 which has the general formula of:

The compounds of the invention as described above can be synthesized using methods, techniques, and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds of the invention and intermediates thereof are commercially available from sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.), or alternatively can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the present compounds and/or starting materials thereof are either described in the art or will be readily apparent to the skilled artisan. Alternatives to the reagents and/or protecting groups may be found in the references provided above and in other compendiums well known to the skilled artisan. In particular, preparation of the present compounds may include one or more steps of protection and de-protection (e.g., the formation and removal of acetal groups). Guidance for selecting suitable protecting groups can be found, for example, in Greene & Wuts, "Protective Groups in Organic Synthesis," Wiley Interscience, 1999. In addition, the preparation may include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ('H and 1 3C NMR), infrared and ultraviolet spectroscopy (IR and UV), X-ray crystallography, elemental analysis (EA), HPLC and mass spectroscopy (MS) can be used as well. The preparation may also involve any other methods of protection and de-protection, purification and identification and quantification that are well known in the chemical arts.

In one embodiment, the antagonist of the NRP-1/OBR signaling pathway is a small organic molecule, which impends the binding of CK2, in particular CK2 alpha to NRP-1 and/or OBR.

In a particular embodiment, the antagonist of the NRP-1/OBR signaling pathway is an inhibitor of CK2 gene expression. An "inhibitor of gene expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of mineralocorticoid receptor mRNA by binding there to and thus preventing protein translation or increasing mRNA degradation, thus decreasing the level of mineralocorticoid receptor, and thus activity, in a cell. For example, antisense oligonucleotides of at least about 15 bases and complementary to unique regions of the mRNA transcript sequence encoding mineralocorticoid receptor can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. Mineralocorticoid receptor gene expression can be reduced by contacting a subject or cell with a small double stranded RNA (dsRNA), or a vector or construct causing the production of a small double stranded RNA, such that mineralocorticoid receptor gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing mineralocorticoid receptor. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

In one embodiment, the agent is an antibody. In particular, the invention embraces antibodies or fragments of antibodies having the ability to block the interaction between NRP-1 and OBR or the interaction between NRP-1 and leptin. The antibodies may have specificity to NRP-1 or OBR. In one embodiment, the antibodies or fragment of antibodies are directed to all or a portion of the extracellular domain of OBR. In one embodiment, the antibodies or fragment of antibodies are directed to an extracellular domain of NRP-1 or OBR. More particularly this invention provides an antibody or portion thereof capable of inhibiting binding of OBR and/or to NRP-1, which antibody binds to an epitope located within a region of OBR or NRP-1, which region of OBR binds to NRP-1. More particularly this invention provides an antibody or portion thereof capable of inhibiting binding of NRP-1 to OBR and/or leptin, which antibody binds to an epitope located within a region of NRP-1, which region of NRP-1 binds to OBR and/or leptin.

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or non human antibody. A non human antibody may be humanized by recombinant methods to reduce its immunogenicity in man.

Typically, antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of NRP-1, or OBR. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the recombinant NRP-1 or OBR may be provided by expression with recombinant cell lines, in particular in the form of human cells expressing NRP-1 or OBR at their surface. Recombinant forms of OBR or NRP-1 may be provided using any previously described method. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., /. *Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/Gen-Pharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In some embodiments, the antibody is a bispecific antibody. The term "bispecific antibody" has its general meaning in the art and refers to any antibody consisting of one binding site for a first target antigen and a second binding site for a second target antigen. In particular, a bispecific antibody according the invention antibody consists of one binding site for NRP-1 and a second binding site for OBR. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-39). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, EMBO J. 10:3655-59. Other examples of bispecific antibodies include Bi-specific T-cell engagers (BiTEs) that are a class of artificial bispecific monoclonal antibodies. BiTEs are fusion proteins consisting of two single-chain variable fragments (scFvs) of different antibodies, or amino acid sequences from four different genes, on a single peptide chain of about 55 kilodaltons. Other bispecific antibodies those described in WO2006064136. In particular the bispecific antibody is a Fab format described in WO2006064136 comprising one VH or VHH specific for NRP-1 and one VH or VHH specific for OBR.

In some embodiments, the antagonist is a polypeptide. In a particular embodiment the polypeptide is a functional equivalent of NRP-1 or OBR. As used herein, a "functional equivalent of NRP-1 or OBR is a compound which is capable of binding to OBR or NRP-1 respectively, thereby preventing its interaction with OBR or NRP-1 or leptin, respectively. The term "functional equivalent" includes fragments, mutants, and muteins of NRP-1 or OBR. The term "functionally equivalent" thus includes any equivalent of NRP-1 or OBR obtained by altering the amino acid sequence, for example by one or more amino acid deletions, substitutions or additions such that the protein analogue retains the ability to bind to OBR or NRP-1 respectively. Amino acid substitutions may be made, for example, by point mutation of the DNA encoding the amino acid sequence. Typically, functional equivalents include molecules that bind OBR or NRP-1 and comprise all or a portion of the extracellular domains of NRP-1 or OBR respectively.

The functional equivalents include soluble forms of NRP-1 or OBR. A suitable soluble form of these proteins, or functional equivalents thereof, might comprise, for example, a truncated form of the protein from which the transmembrane domain has been removed by chemical, proteolytic or recombinant methods.

Typically, the functional equivalent is at least 80% homologous to the corresponding protein. In a preferred embodiment, the functional equivalent is at least 90% homologous as assessed by any conventional analysis algorithm such as for example, the Pileup sequence analysis software (Program Manual for the Wisconsin Package, 1996).

The term "a functionally equivalent fragment" as used herein also may mean any fragment or assembly of fragments of NRP-1 or OBR that binds to OBR or NRP-1 respectively. Accordingly the present invention provides a polypeptide capable of inhibiting binding of OBR to NRP-1, and Leptin to NRP-1, which polypeptide comprises consecutive amino acids having a sequence which corresponds to the sequence of at least a portion of an extracellular domain of OBR, and/or Leptin which portion binds to NRP-1. In one embodiment, the polypeptide corresponds to an extracellular domain of OBR. The present invention also provides a polypeptide capable of inhibiting binding of NRP-1 to OBR an/or Leptin, which polypeptide comprises consecutive amino acids having a sequence which corresponds to the sequence of at least a portion of an extracellular domain of NRP-1, which portion binds to OBR or Leptin. In one embodiment, the polypeptide corresponds to an extracellular domain of NRP-1 or OBR or Leptin.

Functionally equivalent fragments may belong to the same protein family as the human NRP-1 or OBR identified herein. By "protein family" is meant a group of proteins that share a common function and exhibit common sequence homology. Homologous proteins may be derived from non-human species. Preferably, the homology between functionally equivalent protein sequences is at least 25% across the whole of amino acid sequence of the complete protein. More preferably, the homology is at least 50%, even more preferably 75% across the whole of amino acid sequence of the protein or protein fragment. More preferably, homology is greater than 80% across the whole of the sequence. More preferably, homology is greater than 90% across the whole of the sequence. More preferably, homology is greater than 95% across the whole of the sequence.

The polypeptides of the invention may be produced by any suitable means, as will be apparent to those of skill in the art. In order to produce sufficient amounts of the polypeptides for use in accordance with the present invention, expression may conveniently be achieved by culturing under appropriate conditions recombinant host cells containing the polypeptide of the invention. Preferably, the polypeptide is produced by recombinant means, by expression from an encoding nucleic acid molecule. Systems for cloning and expression of a polypeptide in a variety of different host cells are well known. When expressed in recombinant form, the polypeptide is typically generated by expression from an encoding nucleic acid in a host cell. Any host cell may be used, depending upon the individual requirements of a particular system. Suitable host cells include bacteria mammalian cells, plant cells, yeast and baculovirus systems. Mammalian cell lines available in the art for expression of a heterologous polypeptide include Chinese hamster ovary cells. HeLa cells, baby hamster kidney cells and many others. Bacteria are also preferred hosts for the production of recombinant protein, due to the ease with which bacteria may be manipulated and grown. A common, preferred bacterial host is E coli.

In specific embodiments, it is contemplated that polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. In example adding dipeptides can improve the penetration of a circulating agent in the eye through the blood retinal barrier by using endogenous transporters.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 60 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes. Such linkers may be used in modifying the protein or fragment of the protein described herein for therapeutic delivery.

In one embodiment, the agent is an aptamer specific for NRP-1 or OBR and thus impends the formation of the NRP-1/OBR complex. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence.

In some embodiments, the antagonists of the invention are used in combination with a chemotherapeutic agent for the treatment of cancer. Chemotherapeutic agents include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

By a "therapeutically effective amount" is meant a sufficient amount of the antagonist of the invention to treat the diseases at a reasonable benefit/risk ratio applicable to any medical treatment.

It will be understood that the total daily usage of the compounds of the present invention will be decided by the attending physician within the scope of sound medical judgment. The specific therapeutically effective dose level for any particular subject will depend upon a variety of factors including the disease being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The antagonists of the invention are administered as a formulation in association with one or more pharmaceutically acceptable excipients to form pharmaceutical composition.

As used herein, the term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Pharmaceutical compositions suitable for the delivery of compounds of the present invention and methods for their preparation will be readily apparent to those skilled in the art.

In the pharmaceutical compositions of the present invention for oral, sublingual, subcutaneous, intramuscular, intravenous, transdermal, local or rectal administration, the active principle (i.e. a antagonist of the invention), alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In particular, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Antagonists of the invention can be formulated into a composition in a neutral or salt form as above described.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the antagonists of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

Antagonists of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; liposomal formulations; time release capsules; and any other form currently used.

In some embodiments, the antagonist of the NRP-1/OBR signaling pathway is combined with an anti-VEGF agent of the treatment of cancer.

As used herein an "anti-VEGF agent" refers to a molecule that inhibits VEGF-mediated angiogenesis, vasculogenesis, or undesirable vascular permeability. For example, an anti-VEGF therapeutic may be an antibody to or other antagonist of VEGF. An "anti-VEGF antibody" is an antibody that binds to VEGF with sufficient affinity and specificity to be useful in a method of the invention. An anti-VEGF antibody will usually not bind to other VEGF homologues such as VEGF-B or VEGF-C, or other growth factors such as P1GF, PDGF or bFGF. A preferred anti-VEGF antibody is a monoclonal antibody that binds to the same epitope as the monoclonal anti-VEGF antibody A4.6.1 produced by hybridoma ATCC® HB 10709 and is a high-affinity anti-VEGF antibody. A "high-affinity anti-VEGF antibody" has at least 10-fold better affinity for VEGF than the monoclonal anti-VEGF antibody A4.6.1. Preferably the anti-VEGF antibody is a recombinant humanized anti-VEGF monoclonal antibody fragment generated according to WO 98/45331, including an antibody comprising the CDRs or the variable regions of Y0317. More preferably, anti-VEGF antibody is the antibody fragment known as ranibizumab (LUCENTIS®). The anti-VEGF antibody ranibizumab is a humanized, affinity-matured anti-human VEGF Fab fragment. Ranibizumab is produced by standard recombinant technology methods in *E. coli* expression vector and bacterial fermentation. Ranibizumab is not glycosylated and has a molecular mass of ~48,000 daltons. See WO98/45331 and U.S. 2003/0190317. Anti-VEGF agents include but are not limited to bevacizumab (rhuMab VEGF, Avastin®, Genentech, South San Francisco Calif.), ranibizumab (rhuFAb V2, Lucentis®, Genentech), pegaptanib (Macugen®, Eyetech Pharmaceuticals, New York N.Y.), sunitinib maleate (Sutent®, Pfizer, Groton Conn.)

A further object of the present invention relates to a method for the treatment of cancer in a subject in need thereof comprising administering the subject with a therapeutically effective amount of an anti-VEGF agent and with an therapeutically effective amount of a CK2 inhibitor as above described.

A further object of the present invention relates to a method for preventing or reducing the adaptive-evasive response (e.g. metastases, in particular micrometastases) induced by a prolonged exposure to anti-VEGF treatment in a subject suffering from a cancer comprising administering the subject with a therapeutically effective amount of an antagonist of the NRP-1/OBR signaling pathway. In particular, the NRP-1/OBR/Leptin signaling pathway is a CK2 inhibitor. In particular, the subject suffers from breast cancer.

The present invention also relates to a method for screening a plurality of test substances useful for the prevention or treatment of a disease selected from the group consisting of cancers, obesity and obesity related diseases, cachexia, anorexia, ureteral obstructive kidney disease, autoimmune diseases and infectious diseases comprising the steps consisting of (a) testing each of the test substances for its ability to inhibit the NRP-1/OBR/Leptin signaling pathway and (b) and positively selecting the test substances capable of inhibiting said pathway.

In some embodiments, step (a) of the screening method may consist in determining whether the test substances i) inhibits the formation of the complex between NRP-1 with OBR and/or Leptin, in particular inhibits the interaction between the extracellular domains of NRP1 and OBR ii) inhibits the phosphorylation of OBR and NRP1 induced by CK2, iii) inhibits the nuclear translocation of the NRP-1/OBR complex and iv) inhibits the inhibits the expression of the genes which are expressed under control of the NRP-1/OBR/Leptin signaling pathway.

Any method suitable for the screening of protein-protein interactions is suitable. Whatever the embodiment of the screening method, the complete NRP-1 protein, the complete OBR protein or the complete CK2a protein may be used as the binding partners. Alternatively, fragments of NRP-1 protein, OBR protein and CK2a that include the site of interaction may be used as the binding partners.

In some embodiments step a) of the screening method of the invention consists of the following steps:
a1) bringing into contact the test substance to be tested with a mixture of a first NRP-1 polypeptide or a substantially homologous or substantially similar amino acid sequence thereof and (2) a second OBR polypeptide or a substantially homologous or substantially similar amino acid sequence thereof and/or (3) a Leptin polypeptide or substantially homologous or substantially similar amino acid sequence thereof
a2) determining the ability of said test substance to modulate the binding between said NRP-1 polypeptide and said second OBR polypeptide and/or determining the ability of said test substance to modulate the binding between said NRP-1 polypeptide and said second Leptin polypeptide.

In some embodiments step a) of the screening method of the invention consists of the following steps:
a1) bringing into contact the test substance to be tested with a mixture of a first NRP-1 or OBR polypeptide or a substantially homologous or substantially similar amino acid sequence thereof and (2) a second CK2a polypeptide or a substantially homologous or substantially similar amino acid sequence thereof
a2) determining the ability of said test substance to modulate the binding between said NRP-1 or OBR polypeptide and said second CK2α polypeptide.

In some embodiments step a) of the screening method of the invention consists of the following steps:
a1) bringing into contact the test substance to be tested with a mixture of a first NRP-1 or Leptin polypeptide or a substantially homologous or substantially similar amino acid sequence thereof and (2) a second CK2 alpha polypeptide or a substantially homologous or substantially similar amino acid sequence thereof
a2) determining the ability of said test substance to modulate the binding between said NRP-1 or Leptin polypeptide and said second CK2 alpha polypeptide.

In one embodiment the step a2) consists in generating physical values which illustrate or not the ability of said test substance to modulate the interaction between said first polypeptide and said second polypeptide and comparing said values with standard physical values obtained in the same assay performed in the absence of the said test substance. The "physical values" that are referred to above may be of various kinds depending of the binding assay that is performed, but notably encompass light absorbance values, radioactive signals and intensity value of fluorescence signal. If after the comparison of the physical values with the standard physical values, it is determined that the said test substance modulates the binding between said first polypeptide and said second polypeptide, then the candidate is positively selected at step b).

In some embodiments, the compounds that inhibit the interaction between (i) the NRP-1 polypeptide and (ii) the OBR polypeptide or (iii) the Leptin polypeptide encompass those compounds that bind either to the NRP-1 polypeptide or to OBR polypeptide or to Leptin polypeptide and (ii) the CK2α polypeptide encompass those compounds that bind either to the NRP-1 or OBR polypeptide or to CK2α polypeptide, provided that the binding of the said compounds of interest then inhibits the interaction between NRP-1 and OBR or Leptin.

In some embodiments, the compounds that inhibit the interaction between (i) the NRP-1 or OBR or Leptin polypeptide and (ii) the CK2 alpha polypeptide encompass those compounds that bind either to the NRP-1 or OBR polypeptide or to CK2alpha polypeptide, provided that the binding of the said compounds of interest then inhibits the interaction between NRP-1 and OBR and/or functionality of this complex.

In some embodiments, any polypeptide of the invention suitable for the screening method (i.e. NRP-1, OBR or CK2α polypeptides) is labelled with a detectable molecule for the screening purposes.

According to the invention, said detectable molecule may consist of any compound or substance that is detectable by spectroscopic, photochemical, biochemical, immunochemical or chemical means. For example, useful detectable molecules include radioactive substance (including those comprising $^{32}P$, $^{35}S$, $^{3}H$, or $^{125}I$), fluorescent dyes (including 5-bromodesosyrudin, fluorescein, acetylaminofluorene or digoxigenin), fluorescent proteins (including GFPs and YFPs), or detectable proteins or peptides (including biotin, polyhistidine tails or other antigen tags like the HA antigen, the FLAG antigen, the c-myc antigen and the DNP antigen).

According to the invention, the detectable molecule is located at, or bound to, an amino acid residue located outside the said amino acid sequence of interest, in order to minimise or prevent any artefact for the binding between said polypeptides or between the test substance and or any of said polypeptides.

In another particular embodiment, the polypeptides of the invention are fused with a GST tag (Glutathione S-transferase). In this embodiment, the GST moiety of the said fusion protein may be used as detectable molecule. In the said fusion protein, the GST may be located either at the N-terminal end or at the C-terminal end. The GST detectable molecule may be detected when it is subsequently brought into contact with an anti-GST antibody, including with a labelled anti-GST antibody. Anti-GST antibodies labelled with various detectable molecules are easily commercially available.

In another particular embodiment, the polypeptides of the invention are fused with a poly-histidine tag. Said poly-histidine tag usually comprises at least four consecutive hisitidine residues and generally at least six consecutive histidine residues. Such a polypeptide tag may also comprise up to 20 consecutive histidine residues. Said poly-histidine tag may be located either at the N-terminal end or at the C-terminal end In this embodiment, the poly-histidine tag may be detected when it is subsequently brought into contact with an anti-poly-histidine antibody, including with a labelled anti-poly-histidine antibody. Anti-poly-histidine antibodies labelled with various detectable molecules are easily commercially available.

In a further embodiment, the polypeptides of the invention are fused with a protein moiety consisting of either the DNA binding domain or the activator domain of a transcription factor. Said protein moiety domain of transcription may be located either at the N-terminal end or at the C-terminal end. Such a DNA binding domain may consist of the well-known DNA binding domain of LexA protein originating form E. Coli. Moreover said activator domain of a transcription factor may consist of the activator domain of the well-known Gal4 protein originating from yeast.

In one embodiment of the screening method according to the invention, the first polypeptide and the second polypeptide as described above, comprise a portion of a transcription factor. In said assay, the binding together of the first and second portions generates a functional transcription factor that binds to a specific regulatory DNA sequence, which in turn induces expression of a reporter DNA sequence, said expression being further detected and/or measured. A positive detection of the expression of said reporter DNA sequence means that an active transcription factor is formed, due to the binding together of said first polypeptide and second polypeptide.

Usually, in a two-hybrid assay, the first and second portion of a transcription factor consist respectively of (i) the DNA binding domain of a transcription factor and (ii) the activator domain of a transcription factor. In some embodiments, the DNA binding domain and the activator domain both originate from the same naturally occurring transcription factor. In some embodiments, the DNA binding domain and the activator domain originate from distinct naturally occurring factors, while, when bound together, these two portions form an active transcription factor. The term "portion" when used herein for transcription factor, encompass complete proteins involved in multi protein transcription factors, as well as specific functional protein domains of a complete transcription factor protein.

Therefore in one embodiment of the invention, step a) of the screening method of the invention comprises the following steps:
(1) providing a host cell expressing:
    a first fusion polypeptide between (i) the first polypeptide as define above and (ii) a first protein portion of transcription factor
    a second fusion polypeptide between (i) the second polypeptide as defined above and (ii) a second portion of a transcription factor
    said transcription factor being active on DNA target regulatory sequence when the first and second protein portion are bound together and
    said host cell also containing a nucleic acid comprising (i) a regulatory DNA sequence that may be activated by said active transcription factor and (ii) a DNA report sequence that is operatively linked to said regulatory sequence
(2) bringing said host cell provided at step 1) into contact with a test substance to be tested
(3) determining the expression level of said DNA reporter sequence.

The expression level of said DNA reporter sequence that is determined at step (3) above is compared with the expression of said DNA reporter sequence when step (2) is omitted. A different expression level of said DNA reporter sequence in the presence of the test substance means that the said test substance effectively modulates the binding between the NRP-1 polypeptide and the OBR polypeptide and that said test substance may be positively selected a step b) of the screening method.

Suitable host cells include, without limitation, prokaryotic cells (such as bacteria) and eukaryotic cells (such as yeast cells, mammalian cells, insect cells, plant cells, etc.). However preferred host cell are yeast cells and more preferably a Saccharomyces cerevisiae cell or a Schizosaccharomyces pombe cell.

Similar systems of two-hybrid assays are well known in the art and therefore can be used to perform the screening method according to the invention (see. Fields et al. 1989; Vasavada et al. 1991; Fearon et al. 1992; Dang et al., 1991, Chien et al. 1991, U.S. Pat. No. 5,283,173, U.S. Pat. No. 5,667,973, U.S. Pat. No. 5,468,614, U.S. Pat. No. 5,525,490 and U.S. Pat. No. 5,637,463). For instance, as described in these documents, the Gal4 activator domain can be used for performing the screening method according to the invention. Gal4 consists of two physically discrete modular domains, one acting as the DNA binding domain, the other one functioning as the transcription-activation domain. The yeast expression system described in the foregoing documents takes advantage of this property. The expression of a Gal 1-LacZ reporter gene under the control of a Gal4-activated promoter depends on the reconstitution of Gal4 activity via protein-protein interaction. Colonies containing interacting polypeptides are detected with a chromogenic substrate for β-galactosidase. A compete kit (MATCH-MAKER,™) for identifying protein-protein interactions is commercially available from Clontech.

So in one embodiment, the first polypeptide as above defined is fused to the DNA binding domain of Gal4 and the second polypeptide as above defined is fused to the activation domain of Gal4.

The expression of said detectable marker gene may be assessed by quantifying the amount of the corresponding specific mRNA produced. However, usually the detectable marker gene sequence encodes for detectable protein, so that the expression level of the said detectable marker gene is assessed by quantifying the amount of the corresponding protein produced. Techniques for quantifying the amount of mRNA or protein are well known in the art. For example, the detectable marker gene placed under the control of regulatory sequence may consist of the β-galactosidase as above described.

In another one embodiment, step a) comprises a step of subjecting to a gel migration assay the mixture of the first polypeptide and the second polypeptide as above defined, with or without the test substance to be tested and then measuring the binding of the said polypeptides altogether by performing a detection of the complexes formed between said polypeptides. The gel migration assay can be carried out as known by the one skilled in the art.

Therefore in one embodiment of the invention, step a) of the screening method of the invention comprises the following steps:
(1) providing the first polypeptide and the second polypeptide as defined above
(2) bringing into contact the test substance to be tested with said polypeptides
(3) performing a gel migration assay a suitable migration substrate with said polypeptides and said test substance as obtained at step (2)
(4) detecting and quantifying the complexes formed between said polypeptides on the migration assay as performed at step (3).

The presence or the amount of the complexes formed between the polypeptides are then compared with the results obtained when the assay is performed in the absence of the test substance to be tested.

The detection of the complexes formed between the said two polypeptides may be easily performed by staining the migration gel with a suitable dye and then determining the protein bands corresponding to the protein analysed since the complexes formed between the first and the second polypeptides possess a specific apparent molecular weight. Staining of proteins in gels may be done using any well known methods in the art. Suitable gels are well known in the art but it is preferred to use non denaturant gels. In a general manner, western blotting assays are well known in the art and have been widely described.

In a particular embodiment, the protein bands corresponding to the polypeptides submitted to the gel migration assay can be detected by specific antibodies. It may used both antibodies directed against the first polypeptides (e.g. NRP-1 polypeptides) and antibodies specifically directed against the second polypeptides (e.g. OBR polypeptides).

In another embodiment, the said two polypeptides are labelled with a detectable antigen as above described. Therefore, the proteins bands can be detected by specific antibodies directed against said detectable antigen. Preferably, the detectable antigen conjugates to the first polypeptide is different from the antigen conjugated to the second polypeptide. For instance, the first polypeptide can be fused to a GST detectable antigen and the second polypeptide can be fused with the HA antigen. Then the protein complexes formed between the two polypeptides may be quantified and determined with antibodies directed against the GST and HA antigens respectively.

In another embodiment, step a) included the use of an optical biosensor such as described by Edwards et al. (1997) or also by Szabo et al. (1995). This technique allows the detection of interactions between molecules in real time, without the need of labelled molecules. This technique is indeed based on the surface plasmon resonance (SPR) phenomenon. Briefly, a first protein partner is attached to a surface (such as a carboxymethyl dextran matrix). Then the second protein partner is incubated with the previously immobilised first partner, in the presence or absence of the test substance to be tested. Then the binding including the binding level, or the absence of binding between said protein partner is detected. For this purpose, a light beam is directed towards the side of the surface area of the substrate that does not contain the sample to be tested and is reflected by said surface. The SPR phenomenon causes a decrease in the intensity of the reflected light with a combination of angle and wavelength. The binding of the first and second protein partner causes a change in the refraction index on the substrate surface, which change is detected as a change in the SPR signal.

In another one embodiment of the invention, the screening method includes the use of affinity chromatography. Test substances for use in the screening method above can also be selected by any immunoaffinity chromatography technique using any chromatographic substrate onto which (i) the first polypeptide or (ii) the second polypeptide as above defined, has previously been immobilised, according to techniques well known from the one skilled in the art. Briefly, the NRP-1 polypeptide or the OBR polypeptide as above defined may be attached to a column using conventional techniques including chemical coupling to a suitable column matrix such as agarose, Affi Gel®, or other matrices familiar to those of skill in the art. In some embodiment of this method, the affinity column contains chimeric proteins in which the NRP-1 polypeptide or OBR polypeptide as above defined, is fused to glutathion-s-transferase (GST). Then a test substance is brought into contact with the chromatographic substrate of the affinity column previously, simultaneously or subsequently to the other polypeptide among the said first and second polypeptide. The after washing, the chromatography substrate is eluted and the collected elution liquid is analysed by detection and/or quantification of the said later applied first or second polypeptide, so as to determine if, and/or to which extent, the test substance has modulated the binding between (i) first polypeptide and (ii) the second polypeptide.

In another one embodiment of the screening method according to the invention, the first polypeptide and the second polypeptide as above defined are labelled with a fluorescent molecule or substrate. Therefore, the potential alteration effect of the test substance to be tested on the binding between the first polypeptide and the second polypeptide as above defined is determined by fluorescence quantification.

For example, the first polypeptide and the second polypeptide as above defined may be fused with auto-fluorescent polypeptides, as GFP or YFPs as above described. The first polypeptide and the second polypeptide as above defined may also be labelled with fluorescent molecules that are suitable for performing fluorescence detection and/or quantification for the binding between said polypeptides using fluorescence energy transfer (FRET) assay. The first polypeptide and the second polypeptide as above defined may be directly labelled with fluorescent molecules, by covalent chemical linkage with the fluorescent molecule as GFP or YFP. The first polypeptide and the second polypeptide as above defined may also be indirectly labelled with fluorescent molecules, for example, by non covalent linkage between said polypeptides and said fluorescent molecule. Actually, said first polypeptide and second polypeptide as above defined may be fused with a receptor or ligand and said fluorescent molecule may be fused with the corresponding ligand or receptor, so that the fluorescent molecule can non-covalently bind to said first polypeptide and second polypeptide. A suitable receptor/ligand couple may be the biotin/streptavidin paired member or may be selected among an antigen/antibody paired member. For example, a polypeptide according to the invention may be fused to a poly-histidine tail and the fluorescent molecule may be fused with an antibody directed against the poly-histidine tail.

As already specified, step a) of the screening method according to the invention encompasses determination of the ability of the test substance to modulate the interaction between the first polypeptide and the second polypeptide as above defined by fluorescence assays using FRET. Thus, in a particular embodiment, the first polypeptide as above defined is labelled with a first fluorophore substance and the second polypeptide is labelled with a second fluorophore substance. The first fluorophore substance may have a wavelength value that is substantially equal to the excitation wavelength value of the second fluorophore, whereby the bind of said first and second polypeptides is detected by measuring the fluorescence signal intensity emitted at the emission wavelength of the second fluorophore substance. Alternatively, the second fluorophore substance may also have an emission wavelength value of the first fluorophore, whereby the binding of said and second polypeptides is detected by measuring the fluorescence signal intensity emitted at the wavelength of the first fluorophore substance.

The fluorophores used may be of various suitable kinds, such as the well-known lanthanide chelates. These chelates have been described as having chemical stability, long-lived fluorescence (greater than 0,1 ms lifetime) after bioconjugation and significant energy-transfer in specificity bioaffinity assay. Document U.S. Pat. No. 5,162,508 discloses bipyridine cryptates. Polycarboxylate chelators with TEKES type photosensitizers (EP0203047A1) and terpyridine type photosensitizers (EP0649020A1) are known. Document WO96/00901 discloses diethylenetriaminepentaacetic acid (DPTA) chelates which used carbostyril as sensitizer. Additional DPT chelates with other sensitizer and other tracer metal are known for diagnostic or imaging uses (e.g., EP0450742A1).

In a preferred embodiment, the fluorescence assay performed at step a) of the screening method consists of a Homogeneous Time Resolved Fluorescence (HTRF) assay, such as described in document WO 00/01663 or U.S. Pat. No. 6,740,756, the entire content of both documents being herein incorporated by reference. HTRF is a TR-FRET based technology that uses the principles of both TRF (time-resolved fluorescence) and FRET. More specifically, the one skilled in the are may use a HTRF assay based on the time-resolved amplified cryptate emission (TRACE) technology as described in Leblanc et al. (2002). The HTRF donor fluorophore is Europium Cryptate, which has the long-lived emissions of lanthanides coupled with the stability of cryptate encapsulation. XL665, a modified allophycocyanin purified from red algae, is the HTRF primary acceptor fluorophore. When these two fluorophores are brought together by a biomolecular interaction, a portion of the energy captured by the Cryptate during excitation is released through fluorescence emission at 620 nm, while the remaining energy is transferred to XL665. This energy is then released by XL665 as specific fluorescence at 665 nm. Light at 665 nm is emitted only through FRET with Europium. Because Europium Cryptate is always present in the assay, light at 620 nm is detected even when the biomolecular interaction does not bring XL665 within close proximity.

Therefore in one embodiment, step a) of the screening method may therefore comprises the steps consisting of:
(1) bringing into contact a pre-assay sample comprising:
   a first polypeptide fused to a first antigen,
   a second polypeptide fused to a second antigen
   a test substance to be tested
(2) adding to the said pre assay sample of step (2):
   at least one antibody labelled with a European Cryptate which is specifically directed against the first said antigen
   at least one antibody labelled with XL665 directed against the second said antigen
(3) illuminating the assay sample of step (2) at the excitation wavelength of the said European Cryptate
(4) detecting and/or quantifying the fluorescence signal emitted at the XL665 emission wavelength
(5) comparing the fluorescence signal obtained at step (4) to the fluorescence obtained wherein pre assay sample of step (1) is prepared in the absence of the test substance to be tested.

If at step (5) as above described, the intensity value of the fluorescence signal is different (lower or higher) than the intensity value of the fluorescence signal found when pre assay sample of step (1) is prepared in the absence of the test substance to be tested, then the test substance may be positively selected at step b) of the screening method.

Antibodies labelled with a European Cryptate or labelled with XL665 can be directed against different antigens of interest including GST, poly-histidine tail, DNP, c-myc, HA antigen and FLAG which include. Such antibodies encompass those which are commercially available from CisBio (Bedfors, Mass., USA), and notably those referred to as 61GSTKLA or 61HISKLB respectively.

The test substances that have been positively selected at the end of any one of the embodiments of the in vitro screening which has been described previously in the present specification may be subjected to further selection steps in view of further assaying its properties on NRP-1 phosphorylation, OBR phosphorylation, effects on the gene expression mediated by the NRP-1/OBR/Leptin signaling pathway or cellular functions mediated by the NRP-1/OBR/Leptin signaling pathway (e.g. cell migration). Thus the screening method of the present invention further comprises the steps of screening the compounds positively selected at the end of step i) for their abilities to inhibit i) NRP-1 phosphorylation induced by CK2, to inhibit the OBR phosphorylation induced by CK2, to inhibit the translocation of the nuclear NRP-1/OBR complex, to inhibit the gene expression mediated by the NRP-1/OBR/Leptin signaling pathway or to inhibit the cellular functions mediated by the NRP-1/OBR/Leptin signaling pathway (e.g. cell migration).

The invention will be further illustrated by the following figures and examples. However, these examples and figures should not be interpreted in any way as limiting the scope of the present invention.

FIGURES

FIG. 1: Endogenous NRP-1/OBR detection in breast cancer cell line. A-NRP-1 and OBR mRNA detection in MDA-MB231 positive cells compared to T47D negative cells. B. NRP-1/OBR complex detection by Proximity Ligation Assay technology (PLA: Duolink) In whole cell (red dot) and in the nucleus (white dot: merge between red dot and dapi) olink.com/products/duolink/how-use-duolink. NRP-1/OBR complex detection after NRP-1 overexpression in T47Dneg Cells alone or with OBR overexpression: a very low NRP-1/OBR complex detection in empty vector condition (pcDNA3). An increase of NRP-1/OBR complex detection when NRP-1 is overexpressed alone (pcDNA3-NRP-1) or with OBR (pcDNA3NRP-1/OBR). No change in OBR overexpression alone compared to empty vector indicating the specificity of the signal of NRP-1/OBR complex. D. NRP-1/OBR detection by co-immuno-precipitation: in the cytoplasmic fraction (C) and in nuclear fraction (N) in MDA-MB231 compared toT 470.

FIG. 2A-E. NRP-1/OBR complex is dependent of the activity of Protein-kinase CK2: NRP-1 and OBR are both a substrate of the holoenzyme CK2: In vitro phosphorylation of the recombinant full length NRP-1 (A) and the length OBR (B) indicate that the CK2β subunit is indispensable for the CK2 activity. C. Detection of the NRP-1 and CK2β subunit interaction: By using the PLA technology, the in vitro data showing the implication of CK2β subunit in the phosphorylation of NRP-1 by CK2 are in part confirmed in MDA-MB231 cells by the detection of CK2β interaction with NRP-1 as indicated by the duolink (white dot). D. inhibition of the NRP-1/OBR by CX4945, the ATP competitive inhibitor of the CK2 (Phase II Clinical Trial): MDA-MB231 treatment with the CX4945 (504) during 4 h induces a decrease in NRP-1/OBR complex detection by PLA (red dot) and its nuclear localization (white dot) under the leptin stimulation (10 nM). E. inhibition of the NRP-1/

OBR by the simultaneous CK2α and CK2α' expression silencing using siRNA that confirms the CK2 implication In the NRP-1/OBR complex formation and nuclear localization.

Figure 3A:
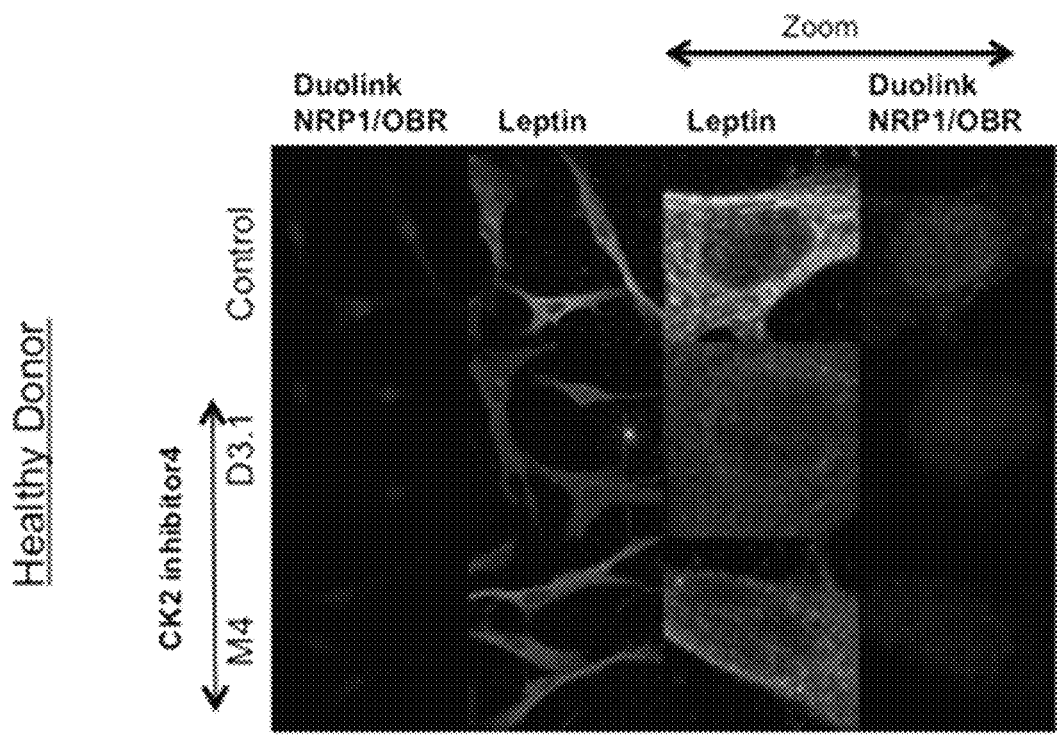
Figure 3B:
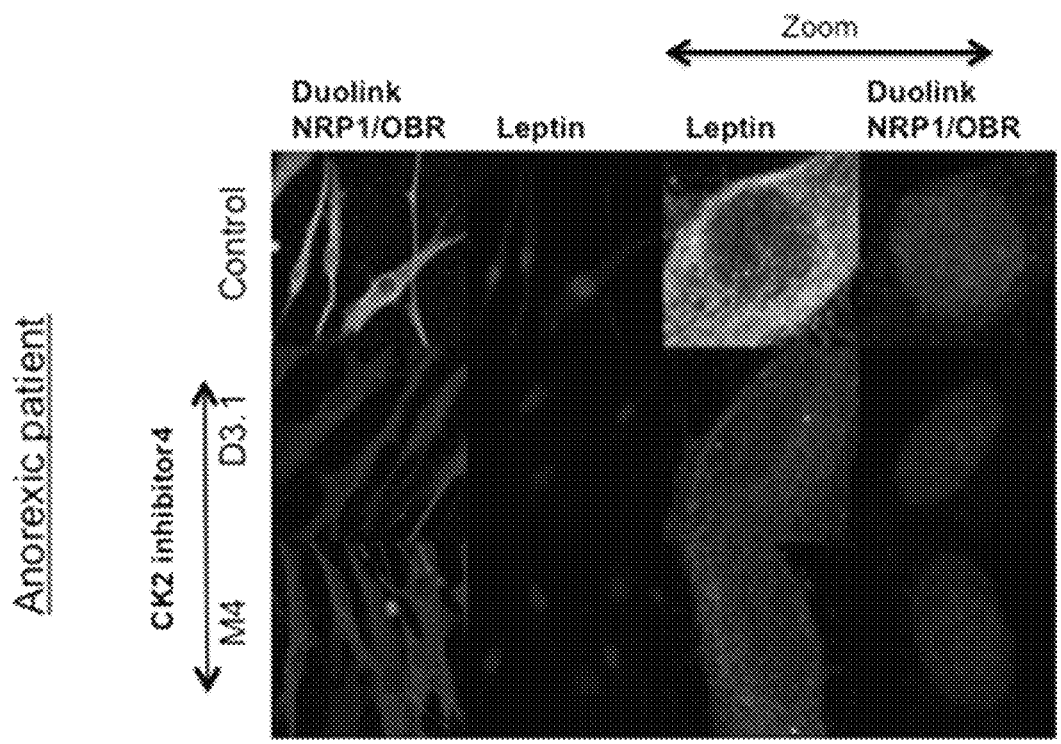

FIG. 3A-B. NRP1/OBR complex formation inhibited by two alosteric inhibitors of Protein-kinase CK2 in skin fibroblast of healthy donor (A) and anorexic patient (B). The NRP-1/OBR complex (Red dot) is detected by de Proximity Ligation assay technology (PLA or Ouolink). Cells were grown in DMEM plus 20% of fetal bovine serum+Sodium pyruvate+LGiutamate and penicillin and streptomycin. Cells were treated or not with D3.1 or M4 CK2 inhibitor during 4 hours. Cells were washed with PBS1X and fixed with iced acetone and rehydrated with PBS before blockage and staining with a Goat ant-Human leptin and Rabbit anti-Neuropilin-1 and Mouse anti-Leptin receptor OBR. Leptin was detected using a donkey and Goat Alexa 488 (Green) and NRP-1 and OBR with anti-Rabbit-PLA minus and antimouse-PLA plus as described in the link indicated above. The NRP-1/OBR complex is inhibited by D3.1 and M4 treatment. The D3.1 seems more efficient. Interestingly, Leptin is also inhibited by CK2 inhibitors.

Figure 4:
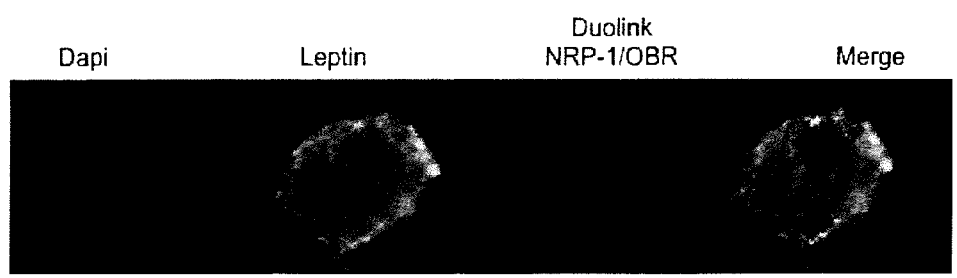
Figure 5A:
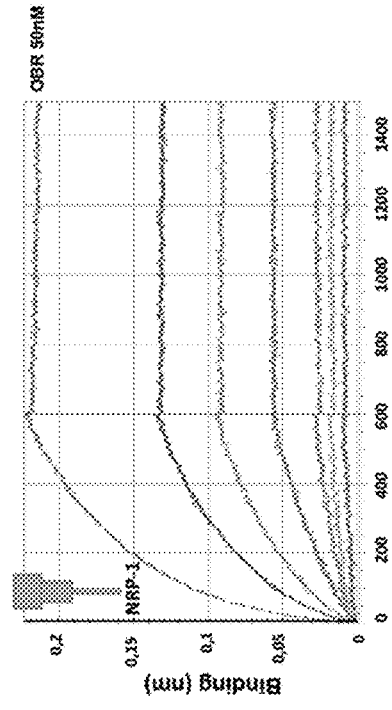
Figure 5B:
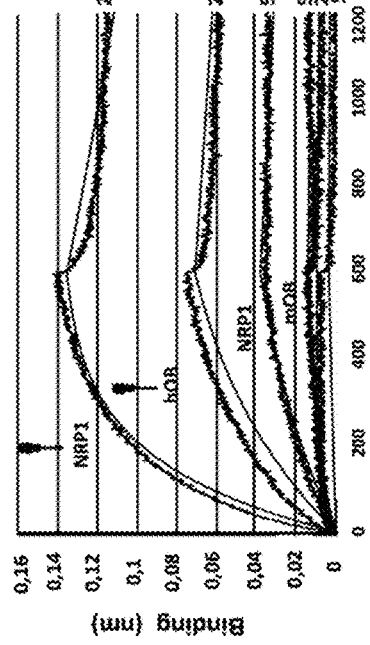
Figure 5C:
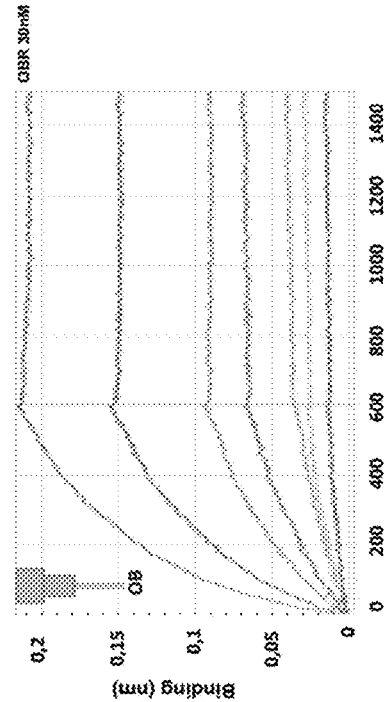
Figure 5D:
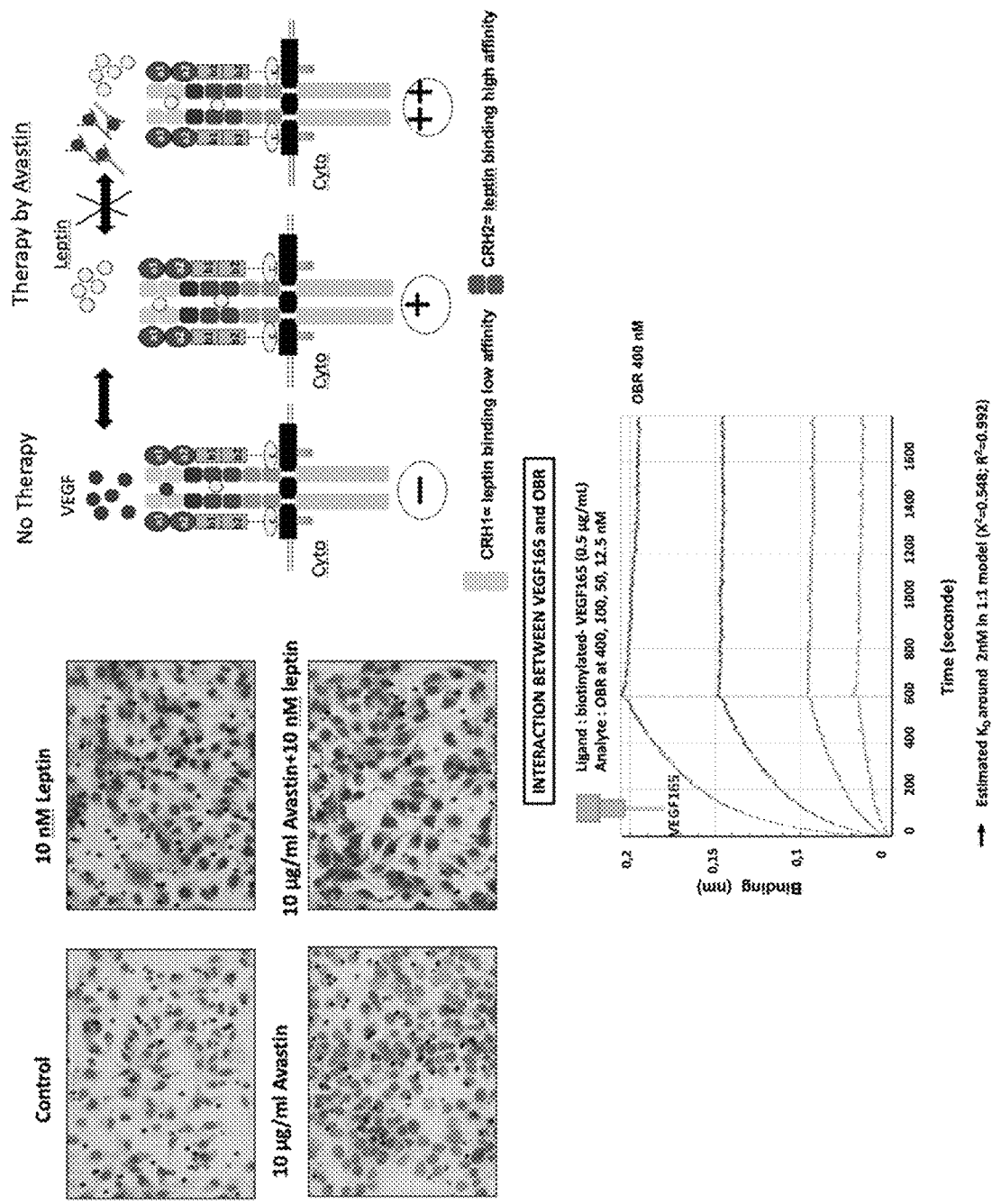

FIG. 4. Leptin and NRP-1/OBR complex detection in the Peripheral Blood Mononuclear Cells (PBMC) of the anorexic patient: Leptin and NRP-1/OBR complex are detected in PBMC freshly isolated from heparinized whole blood by use of Ficoll density gradient centrifugation. As it was observed in MDA-MB231 cells breast cancer cell line and in fibroblasts from healthy donor and anorexic patient, NRP-1/OBR complex is detected in the nucleus. Cells. NRP1/OBR complex is also detected in macrophages of Healthy donor (data not shown}. As is proposed in the patent, NRP-1/OBR could be a target in immune system failure implicating exacerbated Leptin and NRP-1/OBR signaling pathway.

FIG. 5. NRP-1, OBR and leptin interactions confirmation using a Bio-Layer Interferometry (BLI) technology (fortebio.com/bli-technology.html): A-Leptin (OB) interaction to OBR is used as a positive control. Human neuropilin-1 (hNRP-1) interact with human OBR with a high affinity and specifically with human leptin (hOB) but not with murine leptin (mOB). VEGF165 binding to hNRP-1 is used as a positive control. B-Leptin and Avastin association increases MDA-MB231 cells transmigration through 80 μm pore Insert. Avastin treatment may prevent a negative feedback control by VEGF of the pro-angiogenic signaling pathway of Leptin. VEGF binds to OBR which confirms our hypothesis that should be more investigated.

EXAMPLE: 1: NEUROPILIN-1 (NRP-1) INDUCES BREAST CANCER METASTASIS THROUGH ITS NEW PARTNERS LEPTIN/OBR COMPLEX: IDENTIFICATION OF NUCLEAR NRP-1 ASSOCIATED TO GENES SEQUENCES WITH RNA POLYMERASE II AND TRANSCRIPTION FACTOR BINDING SITE

In Vitro and In Vivo Implication of NRP-1 and Leptin in Breast Cancer Cell Line Migration First MBA-MB-231 and T47D breast cancer cells line were selected for their high and undetectable NRP-1 expression respectively and the expression of Leptin receptor (OBR). In order to investigate NRP-1 and Leptin association in breast cancer cell line migration, we proceeded to NRP-1 expression silencing in MDA-MB-231 using either siRNA or shRNA approaches or NRP-1 overexpression in T47D. In contrast to several published data, we were unable to observe MDA-MB-231 and T47D-NRP-1 proliferation under Leptin stimulation. Surprisingly, NRP-1 repression by RNA silencing induces MDA-MD-231 proliferation. In contrast Leptin induced MDA-MB-231 migration that was decreased in siNRP-1 conditions. The in vitro data were confirmed in vivo by MDA-MB-231 and T47D xenografts in Nude mice. Modulation of NRP-1 expression either by shRNA silencing in MDA-MB-231 or by overexpression in T47D induced an increase of proliferation and a decrease of lymph node infiltration by MDA-MB-231-shNRP-1 and a decrease of proliferation and an increase of lymph node infiltration by T47D-NRP-1-RFP in mice treated with Leptin.

Leptin Induces NRP-1/OBR Complex Formation Resulting in OBR Oligomerization (Duolink, HTRF and BRET) and Nuclear Translocation of the Complex.

To confirm a direct association of NRP-1 and Leptin in breast cancer cell migration, we investigated the NRP-1 and OBR interaction by using proximity ligation assay technology (Duolink) in MDA-MB-231 and in T47D-NRP-1. Since OBR is a member of the class I cytokine receptor family, we asked the question if the formation of the complex NRP-1/OBR can or not be modulated by Leptin. This question was investigated endogenously in MDA-MB-231 or by transient transfection of T47D either by NRP-1 or by NRP-1/OBR or OBR alone. After 24 h of transfection, cells were serum starved for 16 h then stimulated with Leptin (10 nM). After 3 h, the stimulation was stopped by removing the medium, cells was first washed then fixed and NRP-1/OBR complex formation was analyzed by Duolink in situ Proximity Ligation Assay (PLA) and by confocal microscopy detection. Co-localization was analyzed using JACoP (ImageJ; National Institutes of Health, Bethesda, Md.) software. Co-localization between molecules was indicated by a positive Pearson coefficient (r). First, the expression of NRP-1 in transfected T47D was confirmed by RT-PCR. NRP-1 forms a complex with endogenous OBR as it is shown by the Duolink detection as red dot in cells transfected with pcDNA3-NRP-1. The Duolink signal increased in the T47D co-transfected with NRP-1 and OBR. The Duolink signals in T47D transfected with either the empty vector pcDNA3 or with the OBR expressing vector were similar. The same results are observed in MDA-MB-231. Surprisingly, the Duolink signal was detected in the nucleus as shown in white dot. By using subcellular protein fractionation kit, NRP-1 and OBR localization in cytoplasmic (C), membrane (M), in the total nuclear extract (N) or in soluble nuclear (SN) and chromatin bound fractions (CB) was analyzed by western blotting either in total lysate or after coimmunoprecipitation. The purity of fraction was assessed by the detection of specific proteins of each fraction such as Hsp90 for the C fraction, SP1 and HDAC2 for the SN and CB fractions and specifically the Calreticulin for endoplasmic reticulum (ER) in order to detect any contamination by the ER membrane fraction in the nuclear fractions. As suspected, OBR was coimmunoprecipitated with NRP-1 in the cytoplasmic (C) and in the nuclear fraction (N) of MDA-MB-231 but not in T47D. As well as Phosphorylated OBR (P-OBR), NRP-1 was detected in cytoplasmic fraction and in nuclear fractions SN and CB of 16 h serum starved MDA-MB-231 and stimulated with 10 nM of Leptin during 3 h at 37° C. The P-OBR and NRP-1 coimmunoprecipitated in the nuclear fractions, increasing with Leptin stimulation as observed by confocal microscopy.

NRP-1/OBR Complex Formation and its Nuclear Translocation Implicate NRP-1 Phosphorylation by Protein-Kinase CK2.

Beside the modulation of the NRP-1/OBR complex formation by Leptin and OBR phosphorylation, we postulated a possible phosphorylation of NRP-1 that can regulate the translocation of the complex to the nucleus. Two putative phosphorylation sites of NRP-1 have been reported with no more investigation. The first one at the extracellular B domain as reported by Shintani et al in 2009 with no antibody available and the second one at the Threonine 916 located in the cytoplasmic domain as it was reported by Kyle et al in 2011. Since a specific antibody against P-NRP-1 at the T916 was available, we investigated by coimmunoprecipitation the detection of P-NRP-1 in MDA-MB-231 after serum starvation and stimulation by Leptin (10 nM). Surprisingly, NRP-1 is phosphorylated upon Leptin stimulation and is located in the nucleus either in the soluble fraction or in chromatin bound fraction with P-OBR. To confirm this phosphorylation state, we investigated the possible implication of a Serine/threonine Kinase CK2 using one of its first chemical inhibitor (DRB). In serum starved condition, P-NRP-1 was detected as polarized spot in the cytoplasm and the nucleus of MDA-MB-231. Interestingly, in the MDA-MB-231 stimulated with Leptin (10 nM), P-NRP-1 was detected as diffuse staining in the nucleus. DRB treatment (5004) of Leptin-stimulated cells led not only to the inhibition of the diffuse nuclear P-NRP-1 staining but also to the decrease of P-NRP-1 polarized spot observed in unstimulated cells. The inhibition was specific since, in stimulated condition combined with DMSO at the same dilution of DRB, we were able to observe a diffuse nuclear P-NRP-1 staining.

NRP-1 phosphorylation by CK2 was confirmed in vitro using recombinant protein and $^{32}$P-ATP. In contrast to soluble form of NRP-1 (data not shown), only full length of NRP-1 was phosphorylated in a CK2α and CK2β dependent manner. Since NRP-1 phosphorylation seems to be induced not only with CK2 but also in response to Leptin stimulation we asked the question if NRP-1/OBR complex stability can be also affected by CK2 inhibition.

The investigation was assessed on MDA-MB-231 stably transfected with lentiviral expressing shNRP-1 plasmid and on T47D stably transduced with retroviral expressing vector for NRP-1-RFP stimulated or not with Leptin combined or not with CK2 inhibitors (DRB or TBB).

As attempted, NRP-1/OBR complex was detected by confocal microscopy after by Duolink in situ Proximity Ligation Assay (PLA) in MDA-MB-231 stimulated with Leptin (10 nM). This detection was also observed in MDA-MB-231-shGFP but very less in MDA-MB-231-shNRP-1 confirming NRP-1 association with OBR. Interestingly the NRP-1/OBR complex formation was inhibited by CK2 inhibitors but not by DMSO. The same effect on NRP-1/OBR complex formation was observed in T47D stably transduced with NRP-1-RFP.

The results were confirmed by silencing CK2 subunits by siRNA in MDA-MB-231. As observed in TBB and DBB treatment, a decrease of CK2 expression induced a decrease of NRP-1/OBR complex formation in MDA-MB-231-siCK2α and MDA-MB-231-siCK2α' but not in MDA-MB-231-wt and MDA-MB-231-siGFP.

Since both NRP-1/OBR complex formation and NRP-1 phosphorylation were abolished by CK2 inhibition, we supposed that OBR signaling pathway could be also affected by CK2 inhibition. As suspected, Leptin induced OBR and STAT3 phosphorylation increase in the cytoplasmic and nuclear fractions that was inhibited by TBB treatment in a dose dependent manner.

NRP-1 Chip-Seq Analysis of Sample Generated from MDA-MB-231 and Transcriptome Analysis of RNA Extracts from T47D-NRP-1 Xenograft LED to Identify Genes Implicated in Breast Cancer Metastasis with Sequences Containing Binding Site of RNA Polymerase II and Transcription Factors and Increased Expression Respectively.

On the basis of the NRP-1 detection in the nucleus and especially in the chromatin bound fraction, we performed a Chip-Seq in 16 h serum starved MDA-MB-231 and treated with increasing doses of Leptin (0, 2 and 10 nM) for 3 hours. Chromatin immunoprecipitation (ChIP) assay was conducted with EZ-Magna ChIP™ A using a purified polyclonal rabbit anti-NRP-1 (a generous gift of Alex Kolodkin team). The samples are designed as follow: input mix comprises input of non stimulated cells (NS), cells stimulated with 2 nM of Leptin and cells stimulated with 10 nM of Leptin. For the IgG control, we analyzed a mixt of chip with IgG control of NS, cells stimulated with 2 nM of leptin and cells stimulated with 10 nM of Leptin. The Chip-Seq analysis can be summarized in 1) mapping of reads on complete genome of *Homo Sapiens* (GRCh37), 2) peak detection and coverage by detecting peaks on the reference genome and computing their coverage in mapped reads consisted in finding region enriched in one of the IP sample (NS, 2 nM and 10 nM of leptin) but absent in both control samples (Input mix and IgG mixt) and 3) normalization and comparison of libraries. The number and percentage of mapped reads for each library were 23'226'278 (79.66%) for NS Chip sample, 25'247'185 (76.13%) for 2 nM Chip sample and 29'694'919 (75.27%) for 10 nM Chip sample. The peak detection was performed with the software SEQMONK. A total of 20'495 peaks were detected and annotated with the closest gene located within 10 kb of each peak. We detected 3,844 peaks at a distance >10 kb from a gene, 13,893 peaks overlapping a gene, 1,336 peaks downstream from a gene <10 kb and 1,422 peaks upstream from a gene >10 kb. Interestingly the number of detected peaks increased with the concentration of Leptin. We consider 3181 genes found in the annotations of the 20'495 peaks from all samples. We then map this set of genes to Gene Ontology terms (GO) database and Pathways from Reactome database, and extract the 50 most represented terms and pathways from this databases. More interestingly, identified pathways are globally known to implicate Leptin and NRP-1 such as signal transduction, metabolism, immune system, axon guidance and metabolism of lipids.

By using ENCODE data at UCSC website, we compared the NRP-1 Chip-Seq to reported transcription factors Chip-Seq. The matched sequences led to identify a binding sequence of 140 transcription factors beside RNA polymerase II (Pol2). The main enriched sequences that overlap the starting site of the genes are those containing binding site of transcription factors known to form a complex with Pol2 such CTCF or those known to be a partner of each other such as c-Myc and Max. Interestingly, the count of the sequence increased with Leptin stimulation but with the maximum reached at 2 nM of Leptin but no significant increase between 2 nM and 10 nM of Leptin. The detection of the Pol2 binding sequence raised the question if NRP-1 forms a complex with Pol2. By using an antibody against a carboxyterminal domain (CTD) of Pol2, we were able to confirm an interaction between NRP-1 and RNA Pol2 as it is shown by Duolink in situ Proximity Ligation Assay with the increasing signal in MDA-MB-231 stimulated with 10 nM of Leptin compared to unstimulated cells. The Duolink results were confirmed by the co-immunoprecipitation of Pol2 with NRP-1 using a Rabbit polyclonal anti-NRP-1.

In order to give a sense to these results in terms of possible implication of NRP-1/OBR/Leptin signaling pathways in the induction of the gene expressions implicated in cell migration, we analyzed a transcriptome of xenografts. Although the Chip-Seq was realized on MDA-MB-231, we opted to realize a transcriptome of T47D overexpressing NRP-1-RFP xenografts compared to T47D-wt and T47D-RFP treated or not with Leptin regarding to the lymph node infiltration induced by the NRP-1 overexpression and its increase by Leptin treatment. To determine any direct association of NRP-1 in gene expression, we realize first a global analysis of transcriptome of T47D-NRP-1 xenografts treated and not treated with Leptin (n=8) compared to T47D-wt and T47D-RFP xenografts treated and not treated with Leptin (n=8). By using Ingenuity Pathways Analysis (IPA), 32 genes implicated in cell movement, invasion and migration of breast cancer cell lines were increased by NRP-1 overexpression and 5 genes were decreased. The maximum increase was observed for lysyl oxidase gene (LOX, fold increase 2.46, p=0.008) and interestingly, the majority of these genes were enriched in the Chip-Seq of MDA-MB-231 as and some of them contained peaks corresponding to transcription factor binding sequence such as SERPINE1 (plasminogen activator inhibitor type 1 gene, fold increase 1.64; p=0.019) for Pol2 binding sequence and BCAR1 (breast cancer anti-estrogen resistance 1 gene, fold increase 1.72; p=0.003) for CTCF binding sequence. The gene expression decrease is observed for TNFSF10 (tumor necrosis factor (ligand) superfamily, member 10, fold decrease 3.05, p=0.034) enriched also in the Chip-Seq but with no transcription factor binding sequence association. The analysis of gene expression in Leptin treated T47D-NRP-1-RFP compared to no treated xenografts, highlighted 66 genes with 31 genes enriched in the Chip-Seq of MDA-MB-231 and that were not detected in T47D-wt and T47D-RFP treated or not with Leptin. Only 4 genes enriched in the Chip-Seq contained peaks associated to transcription factor binding site such as FUS (fused in sarcoma, fold increase 1.79; p=0.045) for Pol2 and C12orf45 (chromosome 12 open reading frame, fold increase 1.29; p=0.03) for CTCF. The Ingenuity Pathway Analysis led to confirm that some genes overexpressed by the expression of NRP-1 in T47D were related to Leptin and CK2 networks such as SERPINE1, IGFBP3 and CD44. Since Plasminogen Activator Inhibitor 1 (PAI.1) related to SERPINE1 gene has been associated to breast cancer invasion and metastasis, we evaluated PAI.1 expression by immunostaining in T47D-NRP-1-RFP xenografts compared to T47D-wt and T47D-RFP. Interestingly, we observe an increase staining of PAI.1 in T47D-NRP-1-RFP xenografts compared to T47D-wt and T47D-RFP and this increase correlated with Leptin treatment.

On the basis of the association of NRP-1 overexpression in T47D in the infiltration of lymph node by T47D-NRP-1-RFP and in the expression increase of genes reported to be implicated in lymph node infiltration in breast cancer such as N-myc downstream regulated 1 (NDRG1, fold increase 1.81; p=0.006) which was also enriched in the Chip-Seq with peaks related to the transcription factor binding sequence of CTCF and p300, we assessed NRP-1/OBR complex by Duolink in situ Proximity Ligation Assay in infiltrated lymph node by T47D-NRP-1-RFP. Interestingly, we were able to detect T47D-NRP-1-RFP cells as shown in red du to the RFP expression either in treated or not treated xenograft by Leptin but with an increase of red cells in treated condition. NRP-1/OBR complex represented by white dot was detected as well as in treated or not treated cells with nuclear localization indicating NRP-1/OBR complex signaling in the infiltrated lymph node.

DISCUSSION

Neuropolin-1 Induced Breast Cancer Migration and Lymph Node Infiltration Through Leptin/OBR Complex.

Several studies have associated NRP-1 in tumor progression and metastasis independently of its known ligand such as VEGFs and Semaphorins. On the basis of our published data on adipocytes role in the regulation of granulopoiesis through NRP-1 and on the growing connection between obesity and cancer progression, we postulated that the adipokine Leptin and its main receptor OBR may be a new partner of NRP-1. To confirm this hypothesis, we opted to investigate NRP-1 and Leptin association in breast cancer cell line migration. MDA-MB-231 and T47D cell lines were selected for high and undetectable expression of NRP-1 respectively but expressing OBR at different level.

Leptin induced in vitro MDA-MB-231 migration that was decreased by NRP-1 repression using siRNA. Lel Xu et al have reported a direct evidence of NRP-1 up-regulation in tumors treated by anti-VEGF (Bevacizumab). Interestingly, Leptin increased MDA-MB-231 migration induced by 10 µg/ml of Bevacizumab. This observation can be a first explanation of breast cancer therapy failure (increase of Progression survival while decreasing overall survival) by Bevacizumad and that was revoked by the FDA (Food and Drugs Administration, US).

This need to be more investigated and may be a new strategy for combined anti-Leptin and anti-VEGF therapies in breast cancer. As demonstrated by lymph node infiltration, NRP-1 implication in breast cancer cell line migration was confirmed in vivo by its overexpression in T47D cell lines known for their negative expression of NRP-1 and by shNRP-1 silencing in MDA-MB-231 known for their high NRP-1 expression and aggressiveness. Leptin treatment significantly increased lymph node infiltration by T47D-NRP-1-RFP stained for the human KL1. However, in contrast to MDA-MB-231-shGFP, Leptin treatment did not increase lymph node infiltration by MDA-MB-231-shNRP-1 as it was evaluated by KL1 staining. In vitro and in vivo data are a direct evidence of NRP-1 and Leptin association in breast cancer cell line migration. This implication of Leptin and NRP-1 are in agreement of published data but with no association between Leptin and NRP-1. Interestingly other studies in other area have reported Leptin, OBR and NRP-1 but with no any evidence of their association as a signaling complex, for example the expression of Leptin and NRP-1 in a case of idiopathic choroidal neovascularization and NRP-1 expression alteration in OBR deficient mice (db/db).

Neuropilin-1 Forms a Complex with OBR and Induces its Oligomerization Through a Direct Binding of Leptin to OBR Andbut not to NRP-1.

A direct association of NRP-1 and Leptin to breast cancer cell lines migrations was confirmed by the detection of NRP-1/OBR complex in MDA-MB-231 and T47D overexpressing NRP-1.

By using a Duolink PLA, we showed that a direct interaction, between NRP-1 and OBR, takes place under Leptin stimulation compared to serum starved and unstimulated cells. This observation is in agreement with OBR propriety as a member of the class I cytokine receptor family which dimerization is dependent on ligand binding. The NRP-1/OBR complex was confirmed by coimmunoprecipitation of NRP-1 and OBR endogenously in MDA-MB-231 and in transfected Hela cells with either OBR-GFP and/or NRP-1. Immunoprecipitation of OBR-GFP using a specific anti-GFP antibody led to NRP-1 detection in NRP-1 and OBR-GFP co-transfection condition but not in Hela cells transfected with NRP-1 alone confirming the specificity of this complex.

NRP-1 has been reported to bind directly VEGF increasing thus the binding affinity of VEGF to its receptor VEGFR2 (ref) and Sema3A enabling thus its binding to Plexin 3A. Our study led us to highlight a new mechanism of NRP-1 function. In contrast to VEGF and Sema3A, Leptin is unable to bind directly to NRP-1 as it is demonstrated by HTRF and confocal microscopy. (show data of direct binding of leptin to NRP1) However, Leptin binding to OBR induces NRP-1/OBR complex formation resulting in physical proximity between NRP-1 and Leptin as it was demonstrated by the energy transfer from NRP-1 to Leptin in HTRF analysis and OBR oligomerization following NRP-1 binding as demonstrated by BRET analysis. NRP-1 repression by siNRP-1 decreased the BRET signal and OBR oligomerization. The consequence of OBR oligomerization can be linked to the acceleration and the increase of leptin/OBR signaling by NRP-1 overexpression as it was demonstrated in PAEC-NRP-1 cells compared to PAEC-wt. The increase of OBR signaling by NRP-1 can explain the metastatic property acquired by T47D overexpressing NRP-1 as demonstrated by the lymph node infiltration and its decrease in MDA-MB-231-shNRP-1.

NRP-1/OBR Complex Formation and its Nuclear Translocation Depend on NRP-1 Phosphorylation by Protein-Kinase CK2.

The Duolink PLA assay revealed by confocal microscopy showed NRP-1/OBR complex in the nucleus as represented in white dot resulting from co-localization analysis of the Duolink in red dot and the DAPI staining of the nucleus using Jacop software. It is for the first time that membrane complex receptors are reported to translocate to the nucleus. This surprising result was confirmed by inhibiting nuclear export of NRP-1/OBR complex using leptomycin B. MDA-MB-231 co-treated with Leptin and leptomycin B showed increased NRP-1/OBR complex detection by Duolink in the nucleus than MDA-MB-231 treated with Leptin alone. The localization of NRP-1 and OBR was confirmed by the detection of NRP-1 and OBR in the nuclear fraction as well as in the soluble form than in the bound to the chromatin. This localization is specific since we do not detect calreticulin that can be from any contamination by the endoplasmic reticulum membrane. Even tough at this level, the function of NRP-1 in the nucleus was not identify, we suggested that nuclear translocation of the NRP-1/OBR complex should be regulated by their phosphorylation. As reported in the literature, NRP-1 can be a target of CK2. By using chemical CK2 inhibitors TBB or DRB, we were able to confirm not only that NRP-1 is a target for CK2-mediated phosphorylation but that this phosphorylation was indispensable for the NRP-1/OBR complex stability and its nuclear translocation as it was demonstrated by using a specific anti-P-NRP-1 and by the Duolink. The immunostaining of P-NRP-1 clearly show NRP-1 translocation depends on its phosphorylated state since in serum starved and unstimulated MDA-MB-231, P-NRP-1 is concentrated in the nuclear periphery. In stimulated condition, we can observe an accumulation of P-NRP-1 in the nucleus while this localization is inhibited by CK2 inhibitors.

To confirm the association of NRP-1 phosphorylation with the NRP-1/OBR complex formation, we tested a clinically used CK2 inhibitor CX4945 and we repressed CK2α and CK2α' subunit in MDA-MB-231 that have shown the same results obtained with TBB and DRB inhibitors. It was already demonstrated that CK2 phosphorylation activity is implicated in the nuclear translocation of phosphorylated proteins with importin (ref). It might be the case of NRP-1.

Neuropilin-1 Chip-Seq Revealed its Association with RNA Polymerase II (Pol2) and Transcription Factors CTCF and p300: Is NRP-1 a Transcription Factor of a Super Activator?

The association of NRP-1 in in vitro and in vivo breast cancer cell migration and its detection in the nucleus of MDA-MB-231 and of T47D-NRP-1-RFP and principally in the chromatin bound fraction raised the question whether NRP-1 can be associated to gene sequences implicated in cell movement, migration and metastasis. The NRP-1 Chip-Seq analysis has clearly shown a correlation between Leptin stimulation and peak number increase which confirmed the association of NRP-1 and OBR signaling. More interestingly, the enriched peaks corresponded to genes related to Leptin functions, which can be another argument for NRP-1/OBR action. Sequence comparison of NRP-1 Chip-Seq and transcription factor Chip-Seq data from the ENCODE project lead to identify sequence binding of RNA polymerase II (Pol2) and transcription factors. The main enriched sequence were for CTCF, TPB (TATA Binding Protein), TAF1 (Transcription initiation factor TFIID subunit 1 or TBP-associated factor 250 kDa), and p300. Interestingly, the number of enriched sequences corresponding to CTCF binding increased approximately at the same level than Pol2 binding sequences which concords with the already reported studies that made a link between Pol2 and CTCF (MOLECULAR AND CELLULAR BIOLOGY, March 2007, p. 1631-1648; Nature, vol 4 7 9 |3 Nov. 2011). The same conclusion can be made for TBP and TAF1 (ref). All these observation conducted us to conclude on the possible role of NRP-1 as transcription factor or activator or super-activator factor but more investigations are needed to confirm this.

Transcriptome Analysis of T47D Stably Overexpressing NRP-1 Revealed Genes Enriched in NRP-1 Chipseq from MDA-MB-231 and Implicated in Cell Movement and Breast Cancer Metastasis.

It was clearly admitted that NRP-1 overexpression results in larger tumors and in Cell motility. However, the molecular mechanisms associated to cell migration and metastasis are not fully elucidated and NRP-1 function independently of its known ligand such as VEGF is also reported. Mikael Klagsbrun team has already shown that the increase in tumor cell migration after NRP-1 overexpression is independent of VEGF and they postulated that NRP-1 overexpression induces downstream genes that are responsible for enhancing cell motility (FASEB. 2000, vol 14).

In our study, by NRP-1 overexpression in T47D and repression in MDA-MB-231 we also observe a correlation between NRP-1 expression and Tumor volume increase or decrease, respectively. Nevertheless, T47D overexpressing NRP-1 xenograft has tumor growth decrease when treated with Leptin as it was observed for the MDA-MB231. This tumor growth decrease induced by Leptin treatment was accompanied by lymph node infiltration that were not observed in NRP-1 repression condition in MDA-MB-231-shNRP-1.

This observation can lead to conclude that NRP-1 induces tumor growth independently of Leptin/OBR pathway and that NRP-1/OBR complex signaling is in a favor of cell movement and migration induction. The implication of Leptin in tumor growth and metastasis has already been studied but the published data are contradictory depending on cancer cell type and model studies. In human colon cancer model, Aparicio T et al have shown that leptin stimulates colon cancer cell proliferation in vitro but does not promote their growth in vivo in two xenograft model (Gut 2005; 54:1136-1145). In our case, in vitro leptin implication in cell growth has been evaluated by different methods. By MTT assay and (H3)-thymidine incorporation and by BrdU incorporation. In all case we were not able to observe a significant increase of cell proliferation and this was confirmed in vivo. In other hand in vitro and in vivo studies have clearly shown leptin-induced cell migration that was induced of repressed by NRP-1 overexpression in T47D or repression in MDA-MB231. On the basis on this observation we focused our transcriptome analysis on the identification of genes that were already associated with breast cancer metastasis and lymph nod infiltration and that are increased by NRP-1 overexpression and by leptin treatment in T47D and more essentially those identified by NRP-1 Chipseq analysis of MDA-MB231. Even the maximum of the fold increase induced by NRP-1 overexpression in T47D was 2,46, interestingly approximately 72% of genes increased by NRP-1 overexpression were enriched by NRP-1 Chipseq and 17% of these enriched genes contained sequences corresponding to RNA polymerase II (Pol2) and transcription factors CTCF, Rad21, SRF, ERalpha and CEBPB binding sequence. Interestingly, these genes were already demonstrated to be modulated either by leptin or by NRP-1. For example SERPINE1 a gene expressing PAI.1 (Plasminogen Activator Inhibitor-1) has been shown to be up-regulated in endothelial cells (Prachi Singh, BBRC, 2010) and its overexpression has been found in many obesity-related types of cancer and is associated with the progression of breast, endometrial, colorectal, thyroid, renal, and prostate cancer (*Cancer Epidemiol Biomarkers Prev* 2009 voir biblio 97-102). It remain to demonstrate clearly the implication of NRP-1/OBR complex action on SERPINE1 promoter activity by identifying the essential sequence of NRP-1/OBR complex in association with Pol2 since the enriched sequence by NRP-1 Chipseq contained Pol2 binding site. Two genes attracted our attention, BCAR1 (Breast cancer anti-estrogen resistance protein 1/p130 (Cas) and PTK2 (Protein tyrosine Kinase 2) that are not only increased by NRP-1 overexpression in T47D but they were enriched by NRP-1 Chipseq with sequences containing transcription factor binding site of CTCF, Rad21, SRF and CEBPB. Interestingly, NRP-1 was demonstrated to regulate endothelial and tumor cell chemotactic migration through p130Cas) pathway (Evans et Al, MOL. CELL. BIOL., 2011).

In conclusion, this study clearly shows NRP-1 as a new co receptor of Leptin and OBRa discovery of leptin receptor (OBR) as a new partner of NRP-1 and that this complex is associated with breast cancer cell growth arrest but increase of lymph node infiltration. More interestingly, this study highlighted an eventual role of NRP-1 and/or NRP-1/OBR complex as transcription factor or activator or super-activator in the regulation of gene expression by interacting with RNAPol2 as demonstrated here and may be with other transcription factors such as CTCF, P300 and TAF1 that remain to be demonstrated. More interestingly, this new data may open a wide field of investigation of NRP-1/OBR complex in cancer, obesity, immune system and diabetes.

REFERENCES

Throughout this application, various references describe the state of the art to which this invention pertains. The disclosures of these references are hereby incorporated by reference into the present disclosure.

The invention claimed is:

1. A method for treating a cancer having cells that express neuropilin-1 (NRP-1)/OBR complex in a subject in need thereof comprising
   determining that the cancer has cells expressing the NRP-1/OBR complex; and
   administering to the subject a therapeutically effective amount of an antagonist of the NRP-1/OBR signaling pathway, wherein the antagonist of the NRP-1/OBR signaling pathway is a CK2 inhibitor such that the CK2 inhibitor inhibits transport of the NRP-1/OBR complex to the nucleus of the cells expressing the NRP-1/OBR complex.

2. The method of claim 1 wherein the CK2 inhibitor is an allosteric CK2 inhibitor.

3. The method of claim 1 wherein the antagonist of the NRP-1/OBR signaling pathway is combined with an anti-VEGF agent.

4. A method for treating a cancer in a subject in need thereof comprising
   determining that the cancer has cells expressing NRP-1/OBR complex; and
   administering to the subject a therapeutically effective amount of an anti-VEGF agent and a therapeutically effective amount of a CK2 inhibitor such that the CK2 inhibitor inhibits transport of the NRP-1/OBR complex to the nucleus of the cells expressing the NRP-1/OBR complex.

* * * * *